US012390334B2

(12) United States Patent
Running et al.

(10) Patent No.: US 12,390,334 B2
(45) Date of Patent: *Aug. 19, 2025

(54) TOTAL REVERSE SHOULDER SYSTEMS AND METHODS

(71) Applicant: Shoulder Innovations, Inc., Grand Rapids, MI (US)

(72) Inventors: Donald E. Running, Holland, MI (US); Robert J. Ball, West Olive, MI (US); Jason Slone, Silver Lake, IN (US)

(73) Assignee: Shoulder Innovations, Inc., Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/064,439

(22) Filed: Feb. 26, 2025

(65) Prior Publication Data

US 2025/0213366 A1 Jul. 3, 2025

Related U.S. Application Data

(63) Continuation of application No. 18/761,202, filed on Jul. 1, 2024, now Pat. No. 12,268,611, which is a
(Continued)

(51) Int. Cl.
*A61F 2/30* (2006.01)
*A61B 17/17* (2006.01)
(Continued)

(52) U.S. Cl.
CPC ........ *A61F 2/4081* (2013.01); *A61B 17/1778* (2016.11); *A61F 2/30749* (2013.01);
(Continued)

(58) Field of Classification Search
None
See application file for complete search history.

(56) References Cited

U.S. PATENT DOCUMENTS

| 2,781,758 A | | 2/1957 | Jacques |
| 3,869,730 A | * | 3/1975 | Skobel ................ A61F 2/30742 |
| | | | 623/19.12 |

(Continued)

FOREIGN PATENT DOCUMENTS

| AU | 2012321093 A1 | 6/2013 |
| AU | 2018251815 | 3/2024 |

(Continued)

OTHER PUBLICATIONS

U.S. Appl. No. 13/018,341, filed Jan. 31, 2011, Gunther.
(Continued)

*Primary Examiner* — Ann Hu
(74) *Attorney, Agent, or Firm* — Knobbe, Martens, Olson & Bear, LLP

(57) ABSTRACT

A reverse shoulder system can include, for example, a glenoid baseplate comprising a longitudinal axis, the glenoid baseplate further including a stem and a central channel within a sidewall of the stem. The stem can include a longitudinal axis. The longitudinal axis of the glenoid baseplate can be angled with respect to the longitudinal axis of the stem, wherein the longitudinal axis of the glenoid baseplate is not perpendicular with respect to the longitudinal axis of the stem. Other components including a glenosphere, tools, and methods of use are also disclosed.

22 Claims, 21 Drawing Sheets

Related U.S. Application Data continuation of application No. 18/605,361, filed on Mar. 14, 2024, now Pat. No. 12,023,254, which is a continuation of application No. 17/435,333, filed as application No. PCT/US2020/022094 on Mar. 11, 2020.

(60) Provisional application No. 62/816,708, filed on Mar. 11, 2019.

(51) Int. Cl.
  *A61B 17/80* (2006.01)
  *A61B 17/86* (2006.01)
  *A61F 2/40* (2006.01)

(52) U.S. Cl.
  CPC .............. *A61F 2002/30616* (2013.01); *A61F 2002/4085* (2013.01)

(56) References Cited

U.S. PATENT DOCUMENTS

| | | |
|---|---|---|
| 3,979,778 A | 9/1976 | Stroot |
| 4,003,095 A | 1/1977 | Gristina |
| 4,012,796 A | 3/1977 | Weisman et al. |
| 4,045,826 A | 9/1977 | Stroot |
| 4,206,517 A | 6/1980 | Pappas et al. |
| 4,261,062 A | 4/1981 | Amstutz et al. |
| 4,404,693 A | 9/1983 | Zweymuller |
| 4,550,450 A | 11/1985 | Kinnett |
| 4,698,063 A | 10/1987 | Link et al. |
| 4,700,660 A | 10/1987 | Levchenko et al. |
| 4,783,192 A | 11/1988 | Wroblewski et al. |
| 4,827,919 A | 5/1989 | Barbarito et al. |
| 4,865,605 A | 9/1989 | Dines et al. |
| 4,908,036 A | 3/1990 | Link et al. |
| 4,964,865 A | 10/1990 | Burkhead et al. |
| 4,986,833 A | 1/1991 | Worland |
| 4,990,161 A | 2/1991 | Kampner |
| 5,030,219 A | 7/1991 | Matsen, III et al. |
| 5,032,132 A | 7/1991 | Matsen, III et al. |
| 5,080,673 A | 1/1992 | Burkhead et al. |
| 5,108,440 A | 4/1992 | Grundei |
| 5,281,226 A | 1/1994 | Davydov et al. |
| 5,282,865 A | 2/1994 | Dong |
| 5,314,479 A | 5/1994 | Rockwood, Jr. et al. |
| 5,314,489 A | 5/1994 | Hoffman et al. |
| 5,344,458 A | 9/1994 | Bonutti |
| 5,358,525 A | 10/1994 | Fox et al. |
| 5,370,694 A | 12/1994 | Davidson |
| 5,429,268 A | 7/1995 | Hale et al. |
| 5,437,677 A | 8/1995 | Shearer et al. |
| 5,462,563 A | 10/1995 | Shearer et al. |
| 5,480,450 A | 1/1996 | James et al. |
| 5,489,309 A | 2/1996 | Lackey et al. |
| 5,489,310 A | 2/1996 | Mikhail |
| 5,507,748 A | 4/1996 | Sheehan et al. |
| 5,507,819 A | 4/1996 | Wolf |
| 5,514,184 A | 5/1996 | Doi |
| 5,549,683 A | 8/1996 | Bonutti |
| 5,593,448 A | 1/1997 | Dong |
| 5,702,447 A * | 12/1997 | Walch ................ A61F 2/4081 606/327 |
| 5,702,486 A | 12/1997 | Craig et al. |
| 5,746,771 A | 5/1998 | Clement, Jr. et al. |
| 5,755,811 A | 5/1998 | Tanamal et al. |
| 5,769,856 A | 6/1998 | Dong et al. |
| 5,800,551 A | 9/1998 | Williamson et al. |
| 5,928,285 A | 7/1999 | Bigliani et al. |
| 6,019,766 A | 2/2000 | Ling et al. |
| 6,037,724 A | 3/2000 | Buss et al. |
| 6,228,119 B1 | 5/2001 | Ondria et al. |
| 6,231,913 B1 | 5/2001 | Schwimmer et al. |
| 6,290,726 B1 | 9/2001 | Pope et al. |
| 6,334,874 B1 | 1/2002 | Tornier et al. |
| 6,364,910 B1 | 4/2002 | Shultz et al. |
| 6,368,353 B1 | 4/2002 | Arcand |
| 6,379,386 B1 | 4/2002 | Resch et al. |
| 6,458,136 B1 | 10/2002 | Allard et al. |
| 6,514,287 B2 | 2/2003 | Ondria et al. |
| 6,520,964 B2 | 2/2003 | Tallarida et al. |
| 6,589,281 B2 | 7/2003 | Hyde, Jr. |
| 6,610,067 B2 | 8/2003 | Tallarida et al. |
| 6,620,197 B2 | 9/2003 | Maroney |
| 6,673,115 B2 | 1/2004 | Resch et al. |
| 6,679,916 B1 | 1/2004 | Frankle et al. |
| 6,679,917 B2 | 1/2004 | Ek |
| 6,699,289 B2 | 3/2004 | Iannotti et al. |
| 6,709,463 B1 | 3/2004 | Pope et al. |
| 6,712,823 B2 | 3/2004 | Grusin et al. |
| 6,761,740 B2 | 7/2004 | Tornier |
| 6,783,549 B1 | 8/2004 | Stone et al. |
| 6,790,234 B1 | 9/2004 | Frankle |
| 6,875,234 B2 | 4/2005 | Lipman et al. |
| 6,953,478 B2 | 10/2005 | Bouttens et al. |
| 7,011,686 B2 | 3/2006 | Ball et al. |
| 7,044,973 B2 | 5/2006 | Rockwood et al. |
| 7,238,089 B2 | 7/2007 | Tsumuraya et al. |
| 7,238,208 B2 | 7/2007 | Camino et al. |
| 7,261,741 B2 | 8/2007 | Weisman et al. |
| 7,294,149 B2 | 11/2007 | Hozack et al. |
| 7,320,709 B2 | 1/2008 | Felt et al. |
| 7,329,284 B2 | 2/2008 | Maroney et al. |
| 7,465,319 B2 | 12/2008 | Tornier |
| 7,517,364 B2 | 4/2009 | Long et al. |
| 7,611,539 B2 * | 11/2009 | Bouttens ............... A61F 2/4637 623/19.11 |
| 7,618,462 B2 | 11/2009 | Ek |
| 7,678,151 B2 | 3/2010 | Ek |
| 7,749,278 B2 | 7/2010 | Frederick et al. |
| 7,753,959 B2 | 7/2010 | Berelsman et al. |
| 7,766,969 B2 * | 8/2010 | Justin .................. A61F 2/389 623/20.15 |
| 7,776,098 B2 | 8/2010 | Murphy |
| 7,892,287 B2 | 2/2011 | Deffenbaugh |
| 7,922,769 B2 | 4/2011 | Deffenbaugh et al. |
| 8,007,538 B2 | 8/2011 | Gunther |
| 8,038,719 B2 | 10/2011 | Gunther |
| 8,048,161 B2 | 11/2011 | Guederian et al. |
| 8,048,167 B2 | 11/2011 | Dietz et al. |
| 8,177,786 B2 | 5/2012 | Leyden et al. |
| 8,303,665 B2 | 11/2012 | Tornier et al. |
| 8,425,614 B2 | 4/2013 | Winslow et al. |
| 8,529,629 B2 | 9/2013 | Angibaud et al. |
| 8,608,805 B2 | 12/2013 | Forrer et al. |
| 8,690,951 B2 * | 4/2014 | Baum .................. A61F 2/4081 623/18.11 |
| 8,721,726 B2 | 5/2014 | Capon et al. |
| 8,778,028 B2 | 7/2014 | Gunther et al. |
| 8,840,671 B2 | 9/2014 | Ambacher |
| 8,870,962 B2 | 10/2014 | Roche et al. |
| 8,920,508 B2 * | 12/2014 | Iannotti ............... A61F 2/30749 623/23.44 |
| 8,940,054 B2 | 1/2015 | Wiley et al. |
| 8,945,229 B2 | 2/2015 | Lappin |
| 9,066,806 B2 | 6/2015 | Phipps |
| 9,114,017 B2 * | 8/2015 | Lappin ................. A61F 2/4603 |
| 9,226,830 B2 | 1/2016 | De Wilde et al. |
| 9,233,003 B2 | 1/2016 | Roche et al. |
| 9,278,005 B2 | 3/2016 | Smits et al. |
| 9,283,083 B2 | 3/2016 | Winslow et al. |
| 9,320,546 B2 | 4/2016 | Keyer et al. |
| 9,381,086 B2 | 7/2016 | Ries et al. |
| 9,414,927 B2 | 8/2016 | Iannotti et al. |
| 9,474,619 B2 | 10/2016 | Reubelt et al. |
| 9,498,344 B2 | 11/2016 | Hodorek et al. |
| 9,498,345 B2 | 11/2016 | Burkhead, Jr. et al. |
| 9,510,952 B2 | 12/2016 | Muir et al. |
| 9,545,311 B2 | 1/2017 | Courtney, Jr. et al. |
| 9,545,312 B2 | 1/2017 | Tornier et al. |
| 9,561,111 B1 * | 2/2017 | Goodman ................. A61F 2/40 |
| 9,610,165 B2 | 4/2017 | Poncet et al. |
| 9,610,166 B2 | 4/2017 | Gunther et al. |
| 9,615,839 B2 | 4/2017 | Olson |

(56) References Cited

U.S. PATENT DOCUMENTS

| | | | |
|---|---|---|---|
| 9,629,725 B2 | 4/2017 | Gargac et al. | |
| 9,693,784 B2 | 7/2017 | Gunther | |
| 9,867,710 B2 | 1/2018 | Dalla Pria et al. | |
| 9,962,265 B2 | 5/2018 | Ek et al. | |
| 9,974,658 B2 | 5/2018 | Chudik | |
| 10,034,753 B2 | 7/2018 | Dressler et al. | |
| 10,123,877 B2 | 11/2018 | Faccioli et al. | |
| 10,143,558 B2 | 12/2018 | Frankle | |
| 10,143,559 B2 | 12/2018 | Ries et al. | |
| 10,357,373 B2* | 7/2019 | Gargac | A61F 2/4081 |
| 10,383,735 B2 | 8/2019 | Wiley et al. | |
| 10,426,625 B2 | 10/2019 | Cardon et al. | |
| 10,492,926 B1 | 12/2019 | Gunther | |
| 10,631,992 B2 | 4/2020 | Hopkins | |
| 10,702,390 B2 | 7/2020 | Chavarria et al. | |
| 10,722,373 B2 | 7/2020 | Hodorek et al. | |
| 10,779,952 B2 | 9/2020 | Gunther et al. | |
| 10,786,265 B2 | 9/2020 | Gunther | |
| 10,813,769 B2 | 10/2020 | Orphanos et al. | |
| 10,856,994 B1 | 12/2020 | Hodorek et al. | |
| 10,925,745 B2 | 2/2021 | Cardon et al. | |
| 10,966,788 B2 | 4/2021 | Britton et al. | |
| 11,007,063 B2 | 5/2021 | Goldberg et al. | |
| 11,065,125 B2 | 7/2021 | Ball | |
| 11,103,357 B2 | 8/2021 | Gargac et al. | |
| 11,166,733 B2 | 11/2021 | Neichel et al. | |
| 11,259,931 B2 | 3/2022 | Pressacco et al. | |
| 11,298,234 B2 | 4/2022 | Wiley et al. | |
| 11,426,283 B2 | 8/2022 | Lefebvre et al. | |
| 11,439,513 B2 | 9/2022 | Lefebvre et al. | |
| 11,464,645 B2 | 10/2022 | Cardon et al. | |
| 11,564,802 B2* | 1/2023 | Ball | A61F 2/4612 |
| D977,643 S | 2/2023 | Ball et al. | |
| 11,571,310 B2 | 2/2023 | Goldberg et al. | |
| 11,596,520 B2 | 3/2023 | Perego et al. | |
| 11,696,772 B2 | 7/2023 | Gunther | |
| 11,771,561 B2* | 10/2023 | Running | A61F 2/4081 623/19.13 |
| 11,957,595 B2 | 4/2024 | Gunther et al. | |
| 11,992,415 B2 | 5/2024 | Gunther et al. | |
| 12,023,254 B1* | 7/2024 | Running | A61F 2/4081 |
| 12,089,859 B2 | 9/2024 | Gunther | |
| 12,109,126 B1 | 10/2024 | Gunther | |
| 12,138,172 B2 | 11/2024 | Ball et al. | |
| 12,268,611 B2* | 4/2025 | Running | A61B 17/1778 |
| 12,310,857 B2 | 5/2025 | Ball | |
| 2001/0011192 A1 | 8/2001 | Ondria et al. | |
| 2001/0037153 A1 | 11/2001 | Rockwood, Jr. et al. | |
| 2001/0047210 A1 | 11/2001 | Wolf | |
| 2002/0055783 A1 | 5/2002 | Tallarida et al. | |
| 2002/0082702 A1 | 6/2002 | Resch et al. | |
| 2002/0087213 A1 | 7/2002 | Bertram, III | |
| 2002/0095214 A1 | 7/2002 | Hyde, Jr. | |
| 2002/0111689 A1 | 8/2002 | Hyde, Jr. et al. | |
| 2002/0120339 A1* | 8/2002 | Callaway | F16C 11/106 623/23.47 |
| 2002/0138148 A1 | 9/2002 | Hyde, Jr. et al. | |
| 2003/0033019 A1 | 2/2003 | Lob | |
| 2003/0100952 A1 | 5/2003 | Rockwood, Jr. et al. | |
| 2003/0114933 A1 | 6/2003 | Bouttens et al. | |
| 2003/0125809 A1 | 7/2003 | Iannotti et al. | |
| 2003/0144738 A1 | 7/2003 | Rogalski | |
| 2003/0158605 A1 | 8/2003 | Tournier | |
| 2003/0163202 A1 | 8/2003 | Lakin | |
| 2003/0236572 A1 | 12/2003 | Bertram, III | |
| 2004/0002766 A1 | 1/2004 | Hunter et al. | |
| 2004/0030400 A1* | 2/2004 | Horber | A61F 2/4014 623/22.44 |
| 2004/0039449 A1 | 2/2004 | Tournier | |
| 2004/0039451 A1 | 2/2004 | Southworth | |
| 2004/0059424 A1 | 3/2004 | Guederian et al. | |
| 2004/0064187 A1 | 4/2004 | Ball et al. | |
| 2004/0064189 A1 | 4/2004 | Maroney et al. | |
| 2004/0064190 A1 | 4/2004 | Ball et al. | |
| 2004/0107002 A1 | 6/2004 | Katsuya | |
| 2004/0122519 A1 | 6/2004 | Wiley et al. | |
| 2004/0122520 A1 | 6/2004 | Lipman et al. | |
| 2004/0167629 A1 | 8/2004 | Geremakis et al. | |
| 2004/0167630 A1 | 8/2004 | Rolston | |
| 2004/0193168 A1 | 9/2004 | Long et al. | |
| 2004/0193275 A1 | 9/2004 | Long et al. | |
| 2004/0193276 A1 | 9/2004 | Maroney et al. | |
| 2004/0193277 A1 | 9/2004 | Long et al. | |
| 2004/0193278 A1 | 9/2004 | Maroney et al. | |
| 2004/0199260 A1 | 10/2004 | Pope et al. | |
| 2004/0220673 A1 | 11/2004 | Pria | |
| 2004/0220674 A1 | 11/2004 | Pria | |
| 2004/0230311 A1 | 11/2004 | Cyprien et al. | |
| 2004/0260398 A1 | 12/2004 | Kelman | |
| 2005/0043805 A1 | 2/2005 | Chudik | |
| 2005/0049709 A1 | 3/2005 | Tornier | |
| 2005/0065612 A1 | 3/2005 | Winslow | |
| 2005/0075638 A1 | 4/2005 | Collazo | |
| 2005/0107882 A1 | 5/2005 | Stone et al. | |
| 2005/0119531 A1 | 6/2005 | Sharratt | |
| 2005/0177241 A1 | 8/2005 | Angibaud et al. | |
| 2005/0261775 A1 | 11/2005 | Baum et al. | |
| 2005/0278030 A1 | 12/2005 | Tornier et al. | |
| 2006/0036328 A1 | 2/2006 | Parrott et al. | |
| 2006/0069443 A1 | 3/2006 | Deffenbaugh et al. | |
| 2006/0069444 A1 | 3/2006 | Deffenbaugh et al. | |
| 2006/0069445 A1 | 3/2006 | Ondrla et al. | |
| 2006/0195194 A1 | 8/2006 | Gunther | |
| 2006/0200249 A1 | 9/2006 | Beguin et al. | |
| 2007/0038302 A1 | 2/2007 | Shultz et al. | |
| 2007/0050042 A1 | 3/2007 | Dietz et al. | |
| 2007/0055380 A1 | 3/2007 | Berelsman et al. | |
| 2007/0112433 A1 | 5/2007 | Frederick et al. | |
| 2007/0118229 A1 | 5/2007 | Bergin et al. | |
| 2007/0156246 A1* | 7/2007 | Meswania | A61F 2/40 623/19.12 |
| 2007/0173945 A1 | 7/2007 | Wiley et al. | |
| 2007/0179624 A1* | 8/2007 | Stone | A61F 2/4081 623/22.36 |
| 2007/0225817 A1 | 9/2007 | Ruebelt et al. | |
| 2007/0225818 A1 | 9/2007 | Reubelt et al. | |
| 2008/0021564 A1 | 1/2008 | Gunther | |
| 2008/0082175 A1 | 4/2008 | Holovacs et al. | |
| 2008/0177327 A1 | 7/2008 | Malandain et al. | |
| 2008/0234820 A1 | 9/2008 | Felt et al. | |
| 2008/0294268 A1 | 11/2008 | Baum et al. | |
| 2009/0105837 A1 | 4/2009 | LaFosse et al. | |
| 2009/0125113 A1 | 5/2009 | Guederian et al. | |
| 2009/0228112 A1 | 9/2009 | Clark et al. | |
| 2009/0270866 A1 | 10/2009 | Poncet | |
| 2009/0281630 A1 | 11/2009 | Delince et al. | |
| 2009/0287309 A1 | 11/2009 | Walch et al. | |
| 2010/0049327 A1 | 2/2010 | Isch et al. | |
| 2010/0087876 A1 | 4/2010 | Gunther | |
| 2010/0087877 A1 | 4/2010 | Gunther | |
| 2010/0114326 A1 | 5/2010 | Winslow et al. | |
| 2010/0161066 A1* | 6/2010 | Iannotti et al. | A61F 2/4081 606/301 |
| 2010/0217399 A1 | 8/2010 | Groh | |
| 2010/0249938 A1 | 9/2010 | Gunther et al. | |
| 2010/0274360 A1 | 10/2010 | Gunther | |
| 2011/0029089 A1* | 2/2011 | Giuliani | A61F 2/40 623/19.14 |
| 2011/0106266 A1 | 5/2011 | Schwyzer et al. | |
| 2011/0112648 A1 | 5/2011 | Gunther | |
| 2011/0137424 A1 | 6/2011 | Lappin et al. | |
| 2011/0144758 A1 | 6/2011 | Deffenbaugh | |
| 2011/0276144 A1 | 11/2011 | Wirth et al. | |
| 2011/0313533 A1 | 12/2011 | Gunther | |
| 2012/0041485 A1 | 2/2012 | Kaiser et al. | |
| 2012/0172996 A1 | 7/2012 | Ries et al. | |
| 2012/0209392 A1 | 8/2012 | Angibaud et al. | |
| 2012/0239156 A1 | 9/2012 | De Wilde et al. | |
| 2012/0253467 A1* | 10/2012 | Frankle | A61F 2/4081 623/19.11 |
| 2013/0060346 A1 | 3/2013 | Collins | |
| 2013/0066433 A1* | 3/2013 | Veronesi | A61F 2/4081 623/19.13 |
| 2013/0090736 A1 | 4/2013 | Katrana et al. | |

(56) References Cited

U.S. PATENT DOCUMENTS

| | | |
|---|---|---|
| 2013/0150972 A1 | 6/2013 | Iannotti et al. |
| 2013/0150975 A1* | 6/2013 | Iannotti et al. ........ A61F 2/4059 623/19.11 |
| 2013/0166033 A1 | 6/2013 | Gunther |
| 2013/0194353 A1 | 8/2013 | Hirai et al. |
| 2013/0197651 A1 | 8/2013 | McDaniel et al. |
| 2013/0261752 A1 | 10/2013 | Lappin et al. |
| 2014/0025173 A1* | 1/2014 | Cardon ................. A61F 2/4081 623/19.13 |
| 2014/0107794 A1 | 4/2014 | Deffenbaugh et al. |
| 2014/0243986 A1 | 8/2014 | Frankle |
| 2014/0253641 A1 | 9/2014 | Furuya |
| 2014/0257499 A1 | 9/2014 | Winslow et al. |
| 2014/0277520 A1 | 9/2014 | Chavarria et al. |
| 2014/0288657 A1 | 9/2014 | Lederman et al. |
| 2015/0105861 A1 | 4/2015 | Gunther et al. |
| 2015/0190237 A1 | 7/2015 | Bonin, Jr. et al. |
| 2015/0223941 A1 | 8/2015 | Lang |
| 2015/0250602 A1 | 9/2015 | Sikora et al. |
| 2015/0265411 A1 | 9/2015 | Deransart et al. |
| 2015/0305877 A1 | 10/2015 | Gargac et al. |
| 2016/0045323 A1 | 2/2016 | Kovacs et al. |
| 2016/0113645 A1 | 4/2016 | Hardy et al. |
| 2016/0270922 A1 | 9/2016 | Pressacco et al. |
| 2016/0302934 A1* | 10/2016 | Chavarria ................. A61F 2/40 |
| 2017/0000617 A1 | 1/2017 | Ries et al. |
| 2017/0042690 A1 | 2/2017 | Burkhead, Jr. et al. |
| 2017/0056187 A1 | 3/2017 | Humphrey et al. |
| 2017/0071749 A1 | 3/2017 | Lappin et al. |
| 2017/0143499 A1 | 5/2017 | Phipps |
| 2017/0202674 A1 | 7/2017 | Gunther et al. |
| 2017/0209275 A1 | 7/2017 | Levy |
| 2017/0273806 A1 | 9/2017 | Cardon et al. |
| 2017/0304063 A1 | 10/2017 | Hatzidakis et al. |
| 2017/0360456 A1 | 12/2017 | Gunther |
| 2018/0008350 A1 | 1/2018 | Varadarajan et al. |
| 2018/0071104 A1 | 3/2018 | Kovacs et al. |
| 2018/0078377 A1 | 3/2018 | Gargac et al. |
| 2018/0161169 A1 | 6/2018 | Cardon et al. |
| 2018/0168815 A1* | 6/2018 | Muir ..................... A61F 2/4684 |
| 2018/0193074 A1 | 7/2018 | Hopkins |
| 2018/0193150 A1 | 7/2018 | Winslow et al. |
| 2018/0200067 A1 | 7/2018 | Axelso, Jr. et al. |
| 2018/0243102 A1 | 8/2018 | Burkhead, Jr. et al. |
| 2018/0333268 A1 | 11/2018 | Cardon et al. |
| 2018/0368982 A1 | 12/2018 | Ball |
| 2019/0336293 A1 | 11/2019 | Kehres |
| 2020/0261209 A1* | 8/2020 | Stchur ................... A61F 2/0811 |
| 2020/0368032 A1 | 11/2020 | Hodorek et al. |
| 2020/0383792 A1 | 12/2020 | Cardon et al. |
| 2021/0038401 A1 | 2/2021 | Ball et al. |
| 2021/0121216 A1 | 4/2021 | Choinski et al. |
| 2021/0137692 A1 | 5/2021 | Budge |
| 2021/0137693 A1 | 5/2021 | Ball et al. |
| 2021/0161675 A1 | 6/2021 | Frankle |
| 2021/0236292 A1 | 8/2021 | Chavarria et al. |
| 2021/0244547 A1 | 8/2021 | Gunther et al. |
| 2021/0251640 A1 | 8/2021 | Gunther |
| 2021/0338446 A1 | 11/2021 | Ball |
| 2022/0125594 A1 | 4/2022 | Frankle et al. |
| 2022/0151795 A1 | 5/2022 | Running et al. |
| 2022/0175543 A1 | 6/2022 | Ball |
| 2022/0175544 A1 | 6/2022 | Ball et al. |
| 2023/0078024 A1 | 3/2023 | Gunther et al. |
| 2023/0080207 A1 | 3/2023 | Gunther et al. |
| 2023/0081505 A1 | 3/2023 | Gunther |
| 2023/0090753 A1 | 3/2023 | Running et al. |
| 2023/0114073 A1 | 4/2023 | Perego et al. |
| 2024/0130862 A1 | 4/2024 | Kiritsis |
| 2024/0188968 A1 | 6/2024 | Gunther |
| 2024/0216144 A1 | 7/2024 | Running et al. |
| 2024/0350276 A1 | 10/2024 | Running |
| 2025/0000662 A1 | 1/2025 | Ball |
| 2025/0177155 A1 | 6/2025 | Ball |

FOREIGN PATENT DOCUMENTS

| | | |
|---|---|---|
| DE | 4220217 | 12/1993 |
| DE | 10164328 A1 | 7/2003 |
| EP | 0299889 A2 | 1/1989 |
| EP | 0339530 A2 | 11/1989 |
| EP | 0570816 A1 | 11/1993 |
| EP | 0 965 312 A1 | 12/1999 |
| EP | 1464305 A1 | 10/2004 |
| EP | 1488764 B1 | 12/2006 |
| EP | 1858453 | 11/2007 |
| EP | 1952788 A1 | 8/2008 |
| EP | 2601912 | 6/2013 |
| EP | 2083759 B1 | 9/2015 |
| EP | 2689750 B1 | 8/2016 |
| EP | 3090705 | 11/2016 |
| EP | 2 787 931 B1 | 3/2018 |
| EP | 3598957 | 7/2018 |
| ES | 2 638 390 T3 | 10/2017 |
| FR | 2248820 A1 | 5/1975 |
| FR | 2567019 A1 | 1/1986 |
| FR | 2695313 A1 | 3/1994 |
| JP | 04-282149 A | 10/1992 |
| JP | 2013-158909 | 8/2013 |
| JP | 2014-515651 | 7/2014 |
| JP | 2017-148558 A | 8/2017 |
| JP | 2017-523872 A | 8/2017 |
| WO | WO 2006/093763 | 8/2006 |
| WO | WO 2008/011078 | 1/2008 |
| WO | WO 2009/071940 | 6/2009 |
| WO | WO 2011/112425 | 9/2011 |
| WO | WO 2013/148437 | 10/2013 |
| WO | WO 2012/075183 | 4/2014 |
| WO | WO 2014/067961 | 5/2014 |
| WO | WO 2014/075037 | 5/2014 |
| WO | WO 2014/195909 | 12/2014 |
| WO | WO 2016/025378 | 2/2016 |
| WO | WO 2017/184792 | 10/2017 |
| WO | WO 2018/022227 | 2/2018 |
| WO | WO 2018/129286 | 7/2018 |
| WO | WO 2018/181420 | 10/2018 |
| WO | WO 2019/006205 | 1/2019 |
| WO | WO 2019/178104 | 9/2019 |
| WO | WO 2019/213073 | 11/2019 |
| WO | WO 2020/023975 | 1/2020 |
| WO | WO-2020104107 A1 * | 5/2020 ........... A61F 2/4081 |
| WO | WO 2020/185893 | 9/2020 |
| WO | WO 2022/187596 | 9/2022 |
| WO | WO 2023/183283 | 9/2023 |
| WO | WO 2024/026101 | 2/2024 |

OTHER PUBLICATIONS

U.S. Appl. No. 13/088,976, filed Apr. 18, 2011, Gunther.
U.S. Appl. No. 16/701,118, filed Dec. 2, 2019, Gunther.
U.S. Appl. No. 18/058,058, filed Nov. 22, 2022, Running et al.
U.S. Appl. No. 29/870,666, filed Feb. 1, 2023, Ball et al.
U.S. Appl. No. 18/349,805, filed Jul. 10, 2023, Gunther.
U.S. Appl. No. 18/477,416, filed Sep. 28, 2023, Running et al.
Biomet, "Absolute™ Bi-Polar." 2001 in 2 pages.
Biomet, "Copeland" ™ Humeral Resurfacing Head, Interlok®/HA Coated Implant Information, 2003 in 1 page.
IBiomet, "Copeland" ™ Humeral Resurfacing Head, 2001 in 12 pages.
Biomet, "Copeland™ Humeral Resurfacing Head, Macrobond™ Implant Information," 2003 in 1 page.
Biomet, "Copeland™ Humeral Resurfacing Head, Surgical Technique," 2003 in 2 pages.
Boileau et al., "The Three-Dimensional Geometry of the Proximal Humerus. Implications for Surgical Technique and Prosthetic Design," J. Bone Joint Surg. Br. 79: 857-865, 1997.
Braun, et al., Modular Short-stem Prosthesis in Total Hip Arthroplasty: Implant Positioning and the Influence of Navigation, Ortho SuperSite (Oct. 2007) in 8 pages.
Clavert et al. Glenoid resurfacing: what are the limits to asymmetric reaming for posterior erosion? J. Shoulder and Elbow Surg. Nov./Dec. 2007: 843-848.

(56) References Cited

OTHER PUBLICATIONS

Dalla Pria, Paolo. Slide presentation, entitled "Shoulder Prosthesis Design and Evolution", to the Naples International Shoulder Congress in Italy (2000) in 55 pages.
DePuy, "Global C.A.P., Surgical Technique Resurfacing Humeral Head Implant," 2004 in 23 pages.
Grainger Catalog No. 400, 2009-2010 ("Grainger"), two pages.
Inset Mini-glenoid Brochure, Titan Modular Shoulder System Brochure, Ascension Orthopedics, 2011, 4 pages.
Karduna et al. Glenhumeral Joint Translations before and after Total Shoulder Arthroplasty. J. Bone and Joint Surg. 79(8) (1997): 1166-1174.
Redacted letter from a third party dated Aug. 24, 2012 in 2 pages.
Levy et al., "Cementless Surface Replacement Arthroplasty of the Should. 5- to 10-year Results with the Copeland Mark-2 Prosthesis," J. Bone Joint Surg. Br. 83: 213-221, 2001.
Lima-Lto Medical Systems Glenoidi/Glenoids catalogue (2001) in 1 page.
Lima-Lto Miniglenoide Cementata document 7560.50.030 (1999) in 1 page.
Panisello, et al., Bone remodelling after total hip arthroplasty using an uncemented anatomic femoral stem: a three-year prospective study using bone densitometry, J Ortho Surg 14(1):32-37 (2006).
Ross, Mark and Duke, Phillip, "Early Experience In The Use of a New Glenoid Resurfacing Technique" Glenoid Presentation, SESA Nov. 4, 2006, Session 4/0800-0930 p. 93 in 1 page.
Tight Fit Tools, Right Angle Drill Attachment, Serial No. 00400 www.tightfittools.com/riganat.html in 1 page/downloaded Mar. 11, 2005.
Titan™ Modular Shoulder System Brochure, 2011, available at http://www.ascensionortho.com/Assets/PDF/TitanModular/TITANModularShoulder_Brochure-revD.pdf (2 pages).
Tournier et al., Enhancement of Glenoid Prosthesis Anchorage using Burying Technique. Techniques in Shoulder & Elbow Surgery 9(1)(2008): 35-42.
USPTO, PTAB, Petition for Post-Grant Review, of U.S. Pat. No. 11,771,561, dated Jul. 3, 2024.
Wang et al., Biomechanical Evaluation of a Novel Glenoid Design in Total Shoulder Arthroplasty. J. Shoulder & Elbow Surgery (2005) 15: 129S-140S.
Webster's Ninth New Collegiate Dictionary "Interface" (1987), three pages.
Statement of Grounds and Particulars of Opposition for Australian Patent Application No. 2006218936 dated Oct. 5, 2012, in 8 pages.
Frankle, et al., "Reverse Shoulder Arthroplasty: Biomechanics, Clinical Techniques, and Current Technologies," 2016. Part 1 of 7.
Frankle, et al., "Reverse Shoulder Arthroplasty: Biomechanics, Clinical Techniques, and Current Technologies," 2016. Part 2 of 7.
Frankle, et al., "Reverse Shoulder Arthroplasty: Biomechanics, Clinical Techniques, and Current Technologies," 2016. Part 3 of 7.
Frankle, et al., "Reverse Shoulder Arthroplasty: Biomechanics, Clinical Techniques, and Current Technologies," 2016. Part 4 of 7.
Frankle, et al., "Reverse Shoulder Arthroplasty: Biomechanics, Clinical Techniques, and Current Technologies," 2016. Part 5 of 7.
Frankle, et al., "Reverse Shoulder Arthroplasty: Biomechanics, Clinical Techniques, and Current Technologies," 2016. Part 6 of 7.
Frankle, et al., "Reverse Shoulder Arthroplasty: Biomechanics, Clinical Techniques, and Current Technologies," 2016. Part 7 of 7.
De Guzman, R.C., "Materials for Orthopedic Applications," In: Li, B., Webster, T. (eds) (2017). Orthopedic Biomaterials, https://doi.org/10.1007/978-3-319-73664-8_14.

* cited by examiner

TOTAL REVERSE SHOULDER SYSTEMS AND METHODS

This application is a continuation of U.S. application Ser. No. 18/761,202, filed on Jul. 1, 2024, which is a continuation of U.S. application Ser. No. 18/605,361, filed Mar. 14, 2024, now U.S. Pat. No. 12,023,254 issued on Jul. 2, 2024, which is a continuation of U.S. application Ser. No. 17/435,333, filed Aug. 31, 2021, which is the national phase of International Application No. PCT/US2020/022094, filed Mar. 11, 2020, which claims the benefit of priority from U.S. Provisional No. 62/816,708, filed Mar. 11, 2019, which are all hereby incorporated by reference in their entireties.

BACKGROUND

Shoulder replacement is a commonly performed medical procedure for treatment of osteoarthritis, rheumatoid arthritis, as well as for treatment of certain deformities related to oncological indications as well as trauma. There are two primary types of articulations available to surgeons for treatment: anatomic and reverse. With anatomic, the surgeon replaces the articular surfaces with industrial materials such that the articulating surfaces are substantially the same shape as the natural anatomy. A stem can be commonly fixed inside the canal of the humerus, a metallic articular head can be rigidly fixed to the proximal aspect of the same, the articular head having a convex articular surface adapted to articulate with the glenoid implant. The glenoid implant can include on its back side (medial side) certain pegs or posts or fins adapted to be rigidly fixed within the glenoid fossa of the scapula and on its front side a concave or flat articular surface adapted to articulate with the humeral head of the humeral implant.

When a reverse prosthesis is used, the articular surface is reversed in that the metallic ball is rigidly fixed to the glenoid fossa of the scapula, and the concave articular surface is rigidly fixed to the humeral bone, thereby reversing the fashion of articulation of the prosthesis.

The surgeon chooses between the two types of prostheses by assessing a number of conditions of the patient including level of pain, patient activity level, deformity or severity of the boney degradation, the strength of surrounding soft tissues, and present or absence of prior surgery, and particularly the health and strength of the rotator cuff muscle and tendon. Disease of the rotator cuff is common among patients with arthritis of the shoulder. In this circumstance, it is commonly observed that the absence of insufficiency of the rotator cuff leads to a condition where the anatomic shoulder replacement prosthesis is not sufficiently stabilized by surrounding soft tissue. In this case, a reverse shoulder replacement prosthesis can be preferred in some cases due to the higher inherent stability of the articulation. In addition, the reverse prosthesis can advantageously utilize the remaining muscles in a way they can be more effective in the absence of the other soft tissue structures by adjusting the position of the articular surfaces within the joint.

SUMMARY

In some embodiments, disclosed herein is a reverse shoulder system, comprising any number of a glenoid baseplate comprising a longitudinal axis, the glenoid baseplate further comprising a stem and a central channel within a sidewall of the stem, the stem comprising a longitudinal axis. The longitudinal axis of the glenoid baseplate can be angled with respect to the longitudinal axis of the stem, wherein the longitudinal axis of the glenoid baseplate is not perpendicular with respect to the longitudinal axis of the stem.

In some configurations, the glenoid baseplate comprises a generally disc-shaped portion extending radially outward from the central channel.

In some configurations, the stem comprises a sidewall that extends superiorly with respect to the disc portion.

In some configurations, the glenoid baseplate comprises a peripheral edge.

In some configurations, the peripheral edge comprises spaced-apart anti-rotation features.

In some configurations, the anti-rotation features comprise slots.

In some configurations, an inferior portion of the peripheral edge comprises a porous coating.

In some configurations, an inferior surface of the generally disc-shaped portion comprises a porous coating, but a superior surface does not comprise a porous coating.

In some configurations, the peripheral edge and/or an inferior surface of the baseplate comprises a conical geometry.

In some configurations, an inferior surface of the baseplate is concave.

In some configurations, the stem comprises a Morse taper lock superior to a superior-most portion of the generally disc-shaped portion of the glenoid baseplate.

In some configurations, the system further comprises a glenosphere.

In some configurations, the glenosphere comprises a superior dome-shaped surface comprising a rotational control feature configured such that an inserter tool can lock the glenosphere and the baseplate to allow for rotation of the glenosphere and the baseplate together.

In some configurations, the rotational control feature comprises a spline.

In some configurations, the system further comprises a central set screw and locking nut.

In some configurations, the system further comprises a central compression screw non-integral with the baseplate and configured for placement adjacent and distal to the central set screw.

BRIEF DESCRIPTION OF THE DRAWINGS

These drawings are illustrative embodiments and do not present all possible embodiments of this invention.

DETAILED DESCRIPTION

In some embodiments, disclosed herein are various embodiments of a total reverse shoulder system, including a variety of humeral trays, humeral bearings, inset glenoid baseplates, threaded locking inserts, and glenospheres. Glenoid surgical techniques are also described, which can utilize various tools including but not limited to sizer/angle guides, stem drill guides, glenoid baseplate inserters, calibrated central drills, peripheral drill guides with fixed or variable angles, central screws, fixed angle peripheral compression screws, variable angle peripheral screws, and glenosphere inserters. Dimensions listed on the accompanying Figures are non-limiting examples only.

Figure 1:
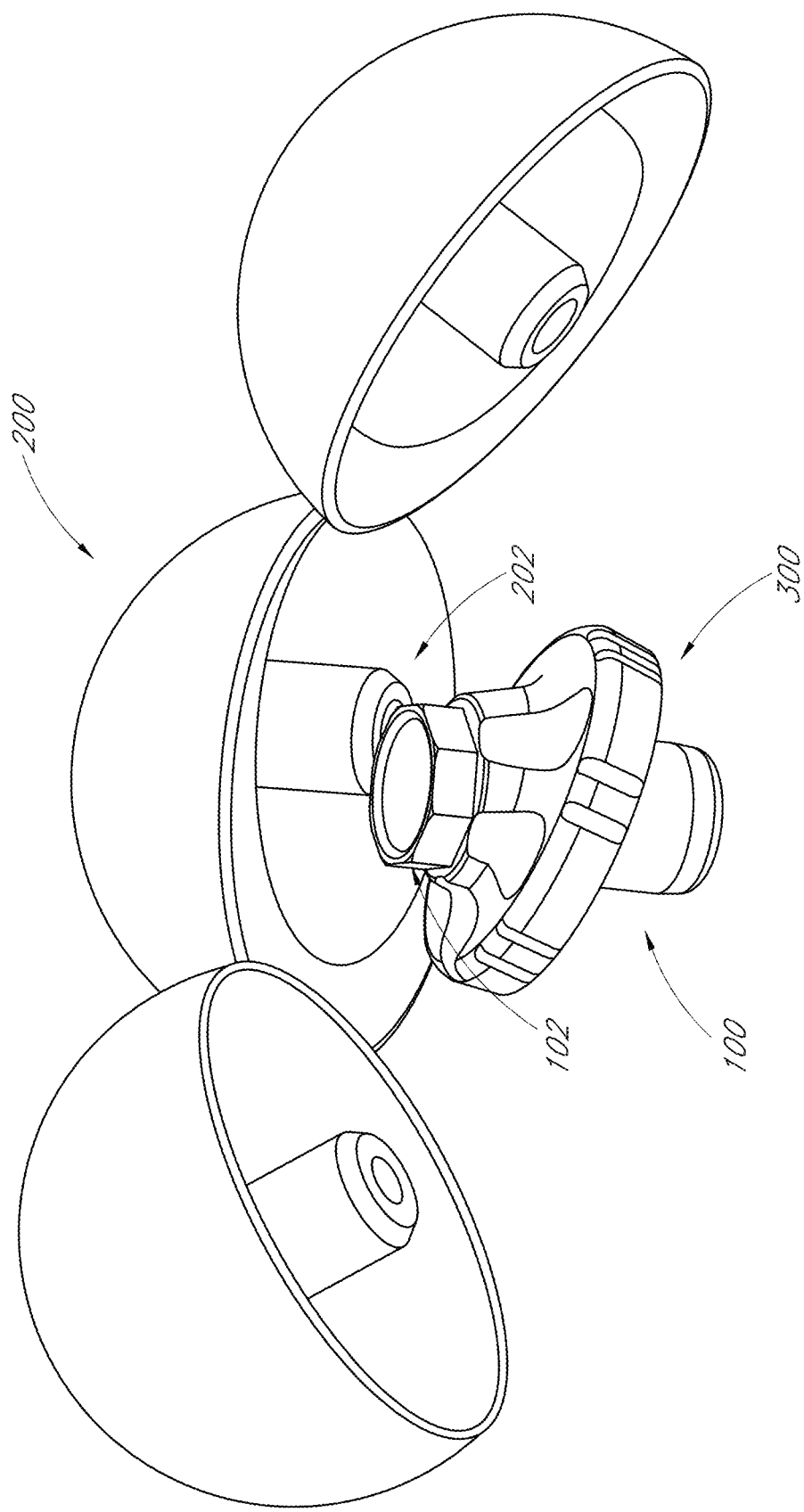
FIG. 1 illustrates an embodiment of components of a total reverse shoulder system.

FIG. 1 illustrates an embodiment of components of a total reverse shoulder system, including a glenosphere 200 and a glenoid baseplate 102 which can be partially or completely inset in some embodiments. The glenoid baseplate 102 can be a generally disc-shaped structure and include a central aperture defining a surface of (e.g., integral with an elongate stem), or configured to fit an elongate stem or post therethrough. The glenoid baseplate 102 can include a longitudinal axis that is at an angle to a longitudinal axis of the elongate stem 100. The longitudinal axis of the glenoid baseplate 102 can be at an angle, such as generally oblique with respect to the longitudinal axis of the elongate stem 100. In some embodiments, the angle is an acute angle, and not a right angle. The angle between the two intersecting longitudinal axes of the respective baseplate 102 and the stem 100 could be, for example, about, at least about, or no more than about 5, 10, 15, 20, 25, 30, 35, 40, 45, 50, 55, 60, 65, 70, 75, 80, 85, 90, or more or less degrees, or ranges including any two of the foregoing values.

Figure 2:
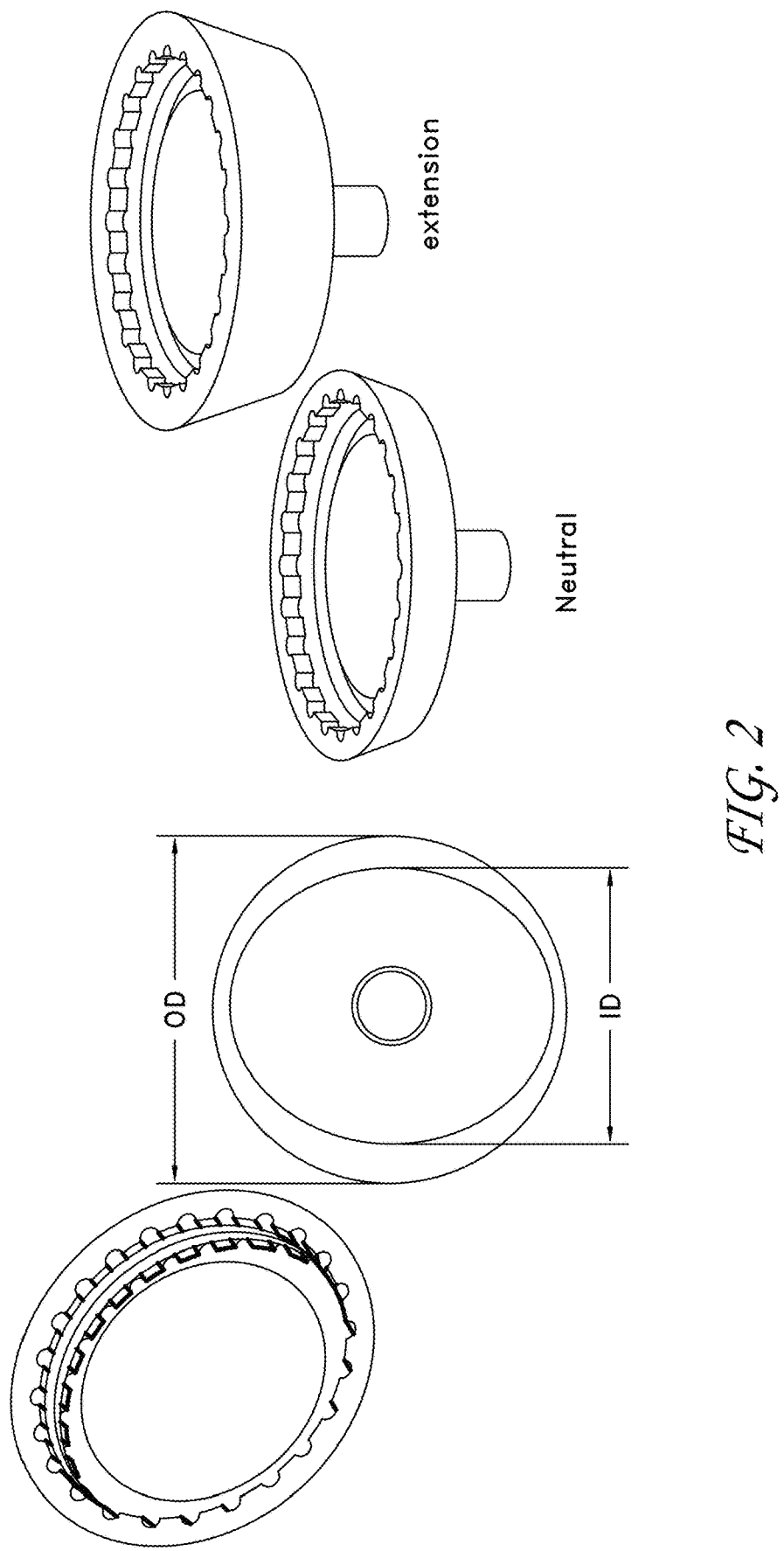
FIG. 2 illustrates various embodiments of humeral trays that can be utilized with total reverse shoulder systems, according to some embodiments.

FIG. 2 illustrates various embodiments of humeral trays that can be utilized with total reverse shoulder systems, according to some embodiments. The humeral trays can include various inner diameters IDs and outer diameters ODs, including 30 mm, 32 mm, 34 mm, 36 mm, 38 mm, 40 mm, 42 mm, or more or less IDs and/or ODs, and ranges including any two of the foregoing values. The trays can include one or more pegs, such as a central peg extending from a medial surface. The trays can be neutral, or include extensions (e.g., in thickness) that can be, for example, +2, 4, 6, 8, 10, 12 mm, or ranges including any two of the foregoing values. The trays can include various cross-sections, including oval or round cross-sections. The trays can be compatible with the same poly bearing surfaces in some cases. In some embodiments, a kit can include at least four different sizes of trays (34 mm oval neutral; 34 mm oval +6 mm extension; 38 mm round neutral; 38 mm round +6 mm extension.

Figure 3:
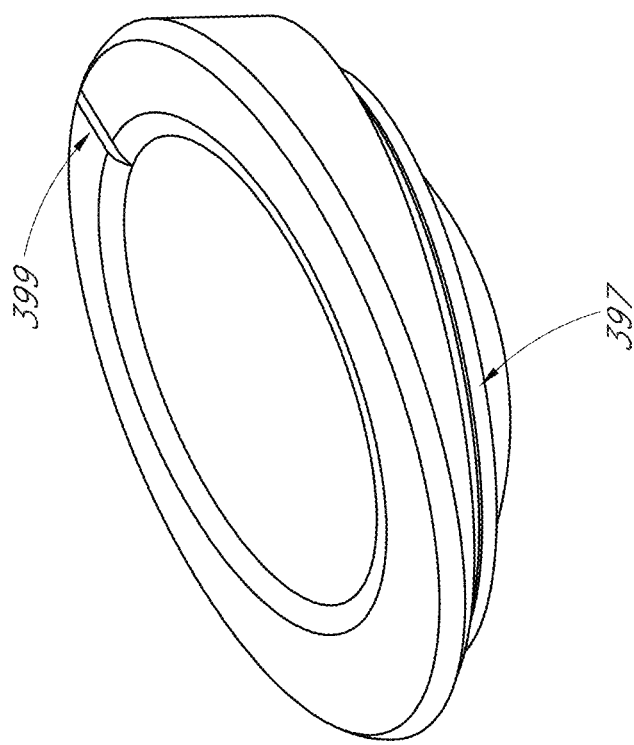
FIG. 3 illustrates a variety of humeral bearing components that can be utilized with total reverse shoulder systems, according to some embodiments.
Figure 3:
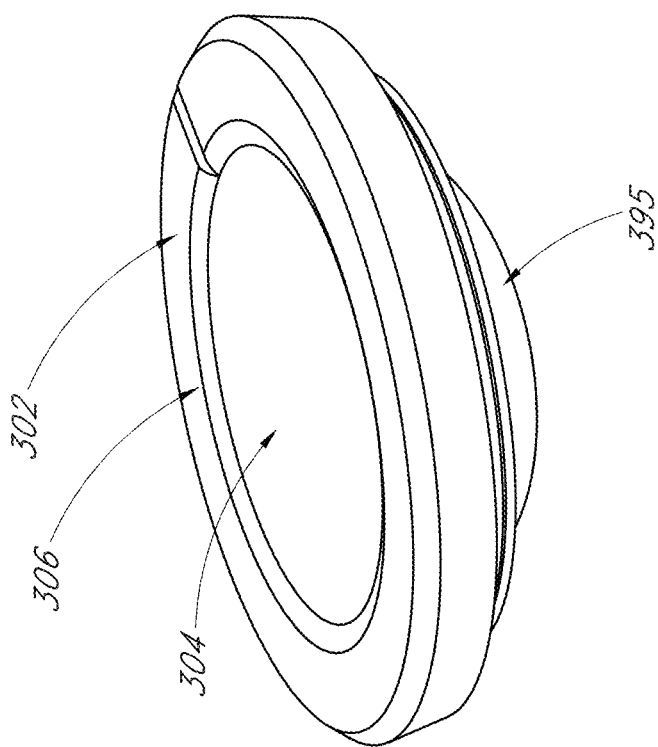

FIG. 3 illustrates a variety of humeral bearing components that can be utilized with total reverse shoulder systems, according to some embodiments, including humeral trays as illustrated and described in connection with FIG. 2. The bearing components can include, for example, a peripheral ring 302 and a central recessed portion that can be outlined radially outwardly by an inner edge of the peripheral ring, and an inner bowl-shaped portion 304. The peripheral ring can include indicia, such as a slot or other marking 399 illustrating the highest point of the bearing component. Also illustrated is the recessed poly dome 395, and a partial or full annular barb 397 around the outer circumference of the bearing component. The bearing component can include a variety of geometries include neutral, 1, 2, 3, 4, 5, 6, 7, 8, 9, 10, 11, 12, 13, 14, 15, 16, 17, 18, 19, 20 degree angles to horizontal, or ranges including any two of the foregoing values. In some embodiments, the bearing component does not change the joint center. In some embodiments, the bearing component can include 30, 31, 32, 33, 34, 35, 36, 37, 38, 39, 40, 41, 42, 43, 44, 45 mm, or more or less spherical diameters, or ranges including any two of the foregoing values. In some embodiments, systems and methods can include an offset of 1, 2, 3, 4, 5, 6, 7, 8, 9, or 10 mm, or ranges including any two of the foregoing values.

Figure 4:
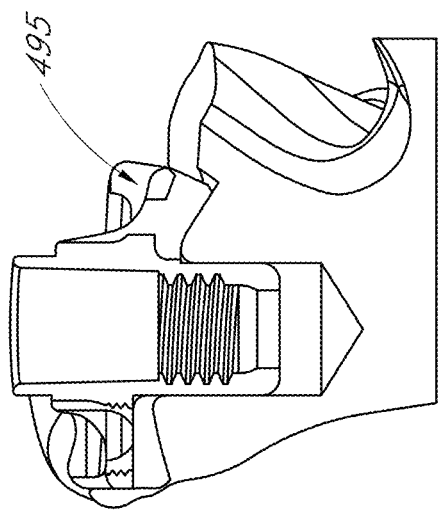
FIG. 4 illustrates schematically an embodiment of a glenoid baseplate configured to be inset into the glenoid.
Figure 4:
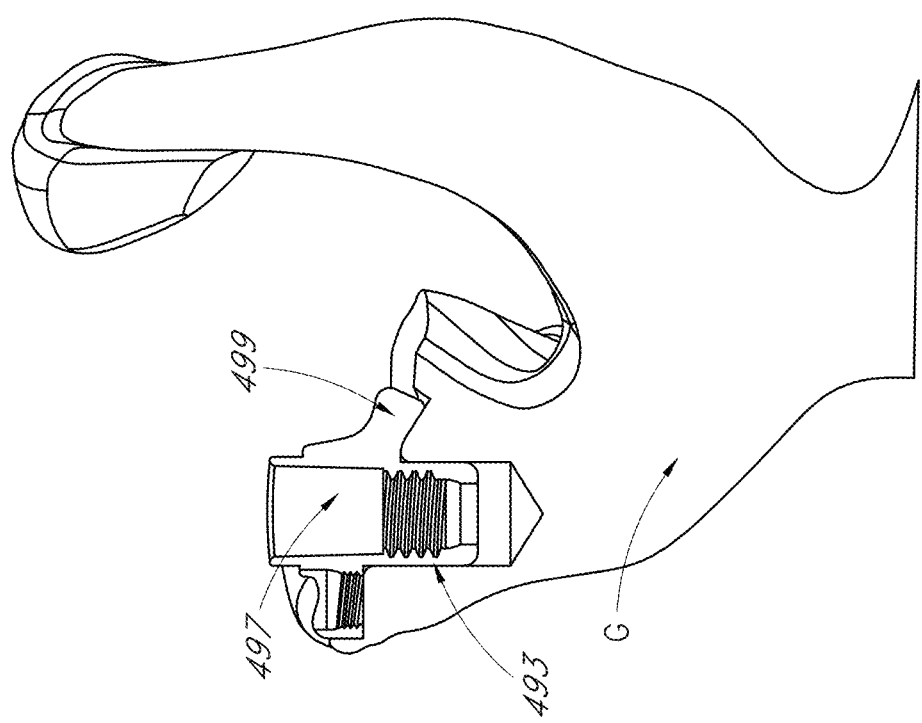

FIG. 4 illustrates schematically an embodiment of a glenoid baseplate configured to be inset into the glenoid G as illustrated. The longitudinal axis of the baseplate can be angled with respect to the longitudinal axis of the stem/post as described, for example, with respect to FIG. 1, and can include a version change 499 to compensate for posterior bony defects. In some embodiments, the glenoid baseplate includes a central channel therethrough defining a surface of (e.g., integral with an elongate stem), or configured to fit configured to house a stem/post as shown. The glenoid baseplate can include a generally conical shape with a concave undersurface configured to rest within a reamed surface of glenoid bone, which advantageously allows for a single rotary reamer to be utilized, in contrast to conventional glenoid baseplates with flat undersurfaces that require a two-step reaming process. The post 493 can have a length of about, at least about, or no more than about 5, 5.5, 6, 6.5, 7, 7.5, 8, 8.5, 9, 9.5, 10, 10.5, 11, 11.5, 12, 12.5, 13, 13.5, 14, 14.5, 15 mm or more or less, or ranges including any two of the foregoing values. In some embodiments, the central channel and/or stem can include a female Morse taper 497 of about 1, 2, 3, 4, 5, 6, 7, 8, 9, 10, or more or less degrees, including ranges incorporating any two of the foregoing values. As shown in the right illustration of FIG. 4, the baseplate can be configured to pivot around the stem/taper at arrow 495 for version correction and to allow for a direct bone-implant interface without requiring augmentation. In some embodiments, the system can be configured to provide version angle corrections of, for example, about 0, 2.5, 5, 7.5, 10, 12.5, 15, 17.5, 20 degrees or more or less, or ranges including any two of the foregoing values. In some embodiments, the baseplate could have a diameter of about, at least about, or no more than about 18, 19, 20, 21, 22, 23, 24, 25, 26, 27, 28, 29, 30, 31, 32, 33, 34, 35, 36, 37, 38, 39, 40 mm, or more or less, or ranges including any two of the foregoing values. The baseplate can advantageously pivot around the central stem with a Morse taper for version correction and allows for a direct bone-implant interface.

Figure 5:
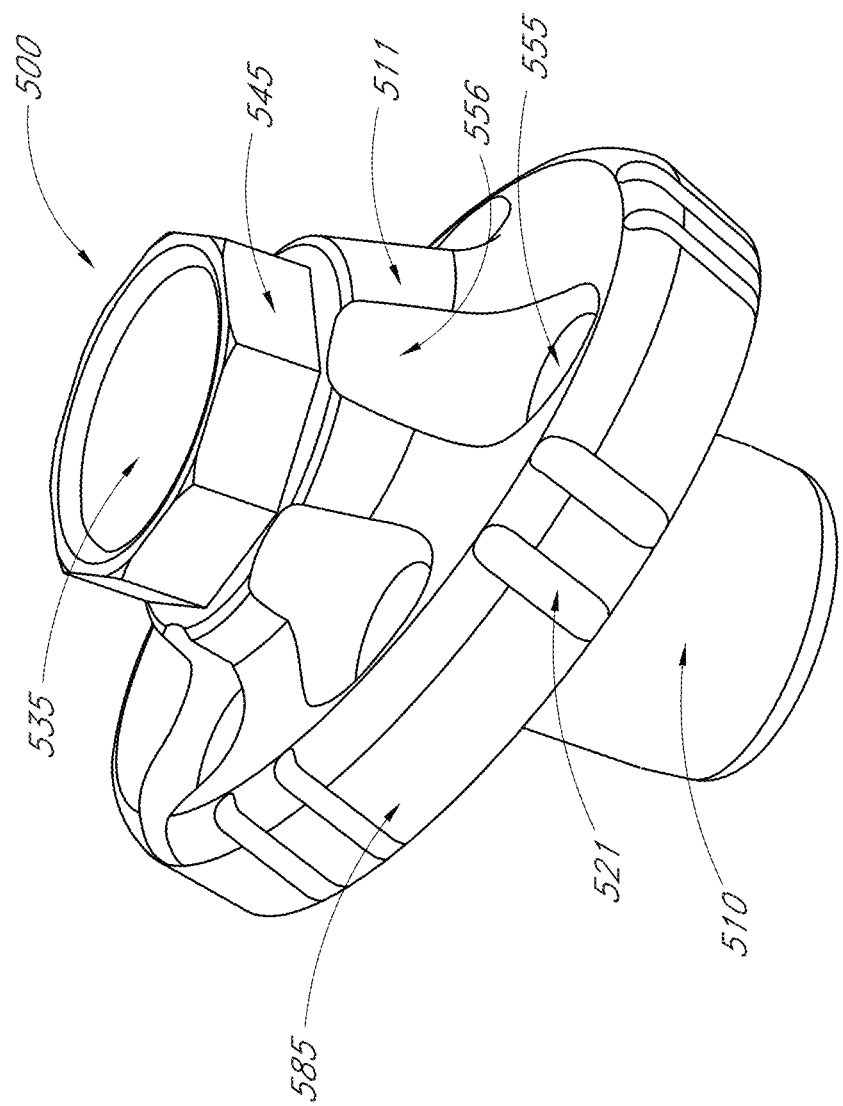
FIG. 5 illustrates schematically an embodiment of a glenoid baseplate 500 configured to be inset into the glenoid.

FIG. 5 illustrates schematically an embodiment of a glenoid baseplate 500 configured to be inset into the glenoid (not shown in FIG. 5). The longitudinal axis of the baseplate 500 can be angled with respect to the longitudinal axis of the stem/post 510 as described, for example, with respect to FIGS. 1 and 4 above. The baseplate 500 could have a generally arcuate peripheral edge. The peripheral edge could include spaced-apart anti-rotational slots 521 directed generally transverse to a longitudinal plane of the baseplate 500. In some embodiments, the peripheral edge of the baseplate 500 can taper (e.g., decrease) in diameter from a superior to inferior dimension. A central channel can extend through the baseplate 500, as well as include a superiorly-extending sidewall or lip 511 somewhat similar to the side slopes of a volcano. The central channel can define a surface of (e.g., integral with an elongate stem), or configured to fit be configured to house the stem/post 510 therethrough. The baseplate 500 can also include a plurality of regularly or irregularly spaced-apart secondary (peripheral) channels 555 spaced radially outward from the central channel of the baseplate and configured to house fixed and variable angle screws therethrough. The secondary channels 555 can be asymmetric and include superiorly-extending portions 556 that can extend into and interrupt the superiorly-extending sidewall or lip 511 of the central channel of the baseplate 500. The baseplate 500 can include a porous coating 585 on the entire, or only a part of the peripheral edge and/or an inferior surface (e.g., undersurface) of the baseplate 500 to promote bone ingrowth, for example.

Still referring to FIG. 5, the stem/post 510 could have an internal taper, such as a Morse taper, of about, at least about, or no more than about 1, 2, 3, 4, 5, 6, 7, 8, 9, 10, 11, 12, 13, 14, 15 degrees, or more or less, or ranges including any two of the foregoing values. The stem/post 510 can also include a rotational control feature 545 along an outer diameter of the stem/post 510, and in some embodiments superiorly with respect to the uppermost surface of the sidewall 511 of the central channel of the glenoid baseplate 500 as shown. The rotational control feature 545 could be non-circular or non-arcuate, such as a hexagonal shape as shown for example. The stem/post 510 can also include a central channel and include a Morse taper lock 535 configured to mate with a glenosphere (not shown). The Morse taper lock can extend superiorly with respect to the uppermost surface of the sidewall 511 of the central channel of the glenoid baseplate 500. The central channel of the stem/post 510 can be configured to house a primary screw (not shown) therethrough, which can be a variable angle primary screw, and optionally locking.

Figure 6:
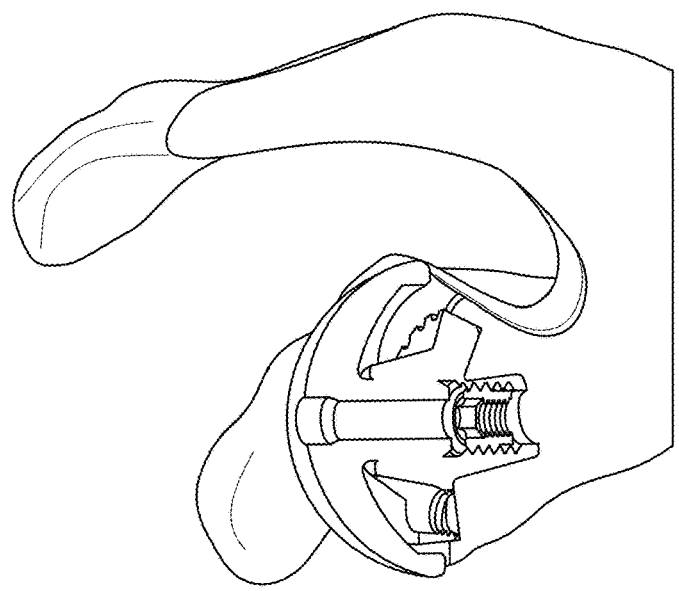
FIG. 6 illustrates a threaded locking insert for a central channel of a stem/post, according to some embodiments.
Figure 6:
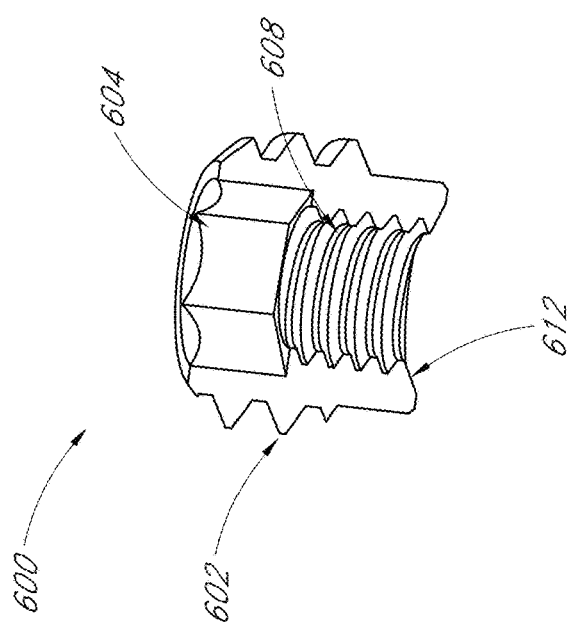
Figure 6:
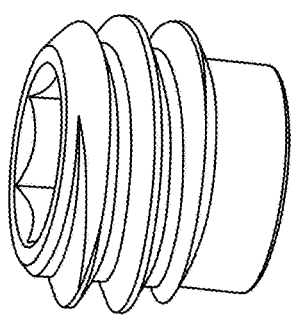

FIG. 6 illustrates a threaded locking insert 600 for a central channel of a stem/post, according to some embodiments. The insert 600 can include an outer male thread 602 and configured to go into the central channel of a baseplate. The outer diameter of the insert can also include a hexagonal geometry portion 604 at the superior end, of about, at least about, or no more than about 1, 2, 3, 4, 5, 6, 7, 8, 9, 10 mm or more or less, or ranges including any two of the foregoing values. The hexagonal geometry portion 604 can be configured to serve as a rotational control feature in some embodiments. The insert 600 can also include a female thread 608 configured to receive a supplemental glenosphere locking screw (not shown) and a spherical surface 612, for example, at its inferior end to lock a variable angle screw.

Figure 7:
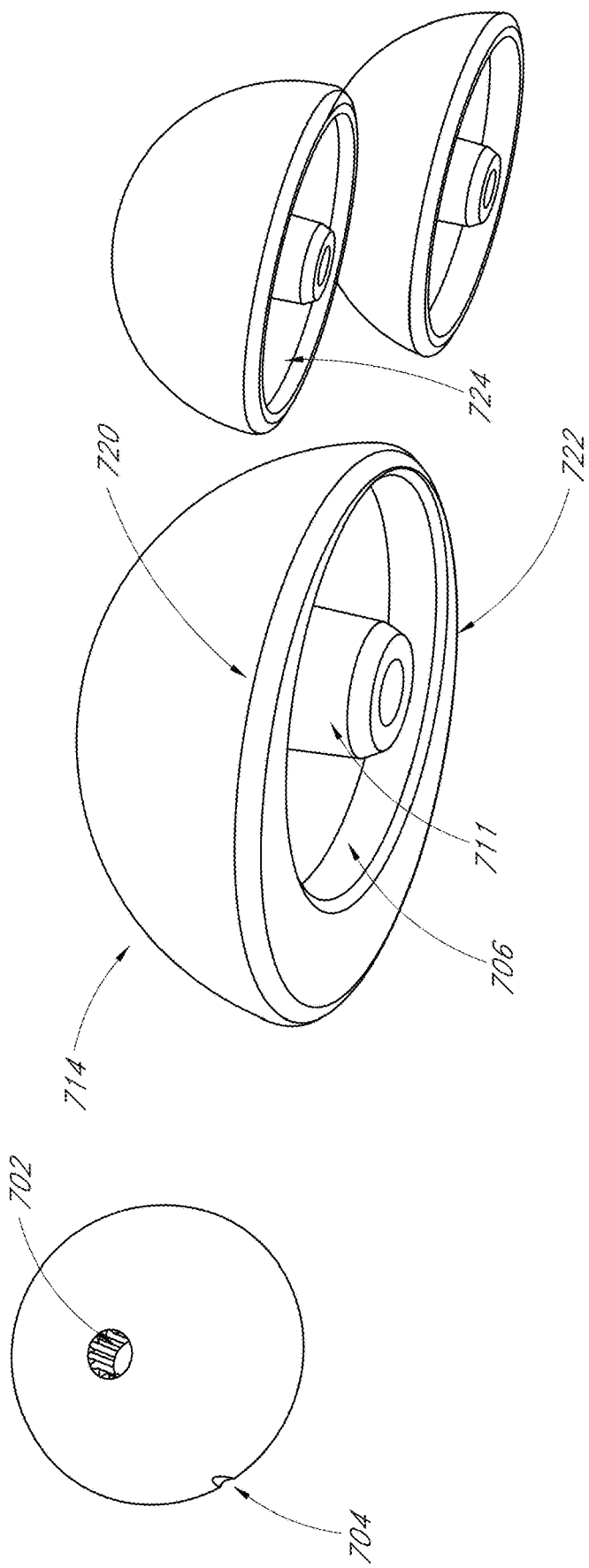
FIG. 7 illustrates various views of glenospheres, according to some embodiments.

FIG. 7 illustrates various views of glenospheres, according to some embodiments. The left image illustrates a glenosphere with a rotational control feature 702, which can include a spline, such as an asymmetric spline, and configured to advantageously allow for rotational control about the spline and allow an inserter tool to lock and rotate the glenosphere together with another component, such as a baseplate. The glenosphere can also include one or more indicia, such as an eccentric rotational mark 704. The glenosphere can include a generally dome-shaped surface 714, a cavity 706 with an inferior-facing opening 708, and a hollow post including a morse taper lock 711 into the baseplate. The glenosphere could be a full hemisphere, or short of a full hemisphere by a distance 720 of about, at least about, or no more than about 0.5 mm, 0.75 mm, 1 mm, 1.25 mm, 1.5 mm, 1.75 mm, 2 mm, 2.25 mm, 2.5 mm, 2.75 mm, 3 mm, or more or less, or ranges including any two of the foregoing values.

Still referring to FIG. 7, in some embodiments, the glenosphere can include an articulating diameter of about, at least about, or no more than about 25, 26, 27, 28, 29, 30, 31, 32, 33, 34, 35, 36, 37, 38, 39, 40, 41, 42, 43, 44, 45, 46, 47, 48, 49, 50 mm, or more or less, or ranges including any two of the foregoing values. In some embodiments, systems and methods can include an offset and/or eccentric dimension of 1, 2, 3, 4, 5, 6, 7, 8, 9, or 10 mm, or ranges including any two of the foregoing values. In some embodiments, the glenosphere has a neutral geometry. In some embodiments, a glenosphere 724 is offset by about +3 mm or about 6 mm, for example. In some embodiments, a glenosphere 722 has an eccentric dimension of between about 2 mm and about 4 mm. In some embodiments, a secondary locking screw can be utilized together with the glenosphere.

Figure 8:
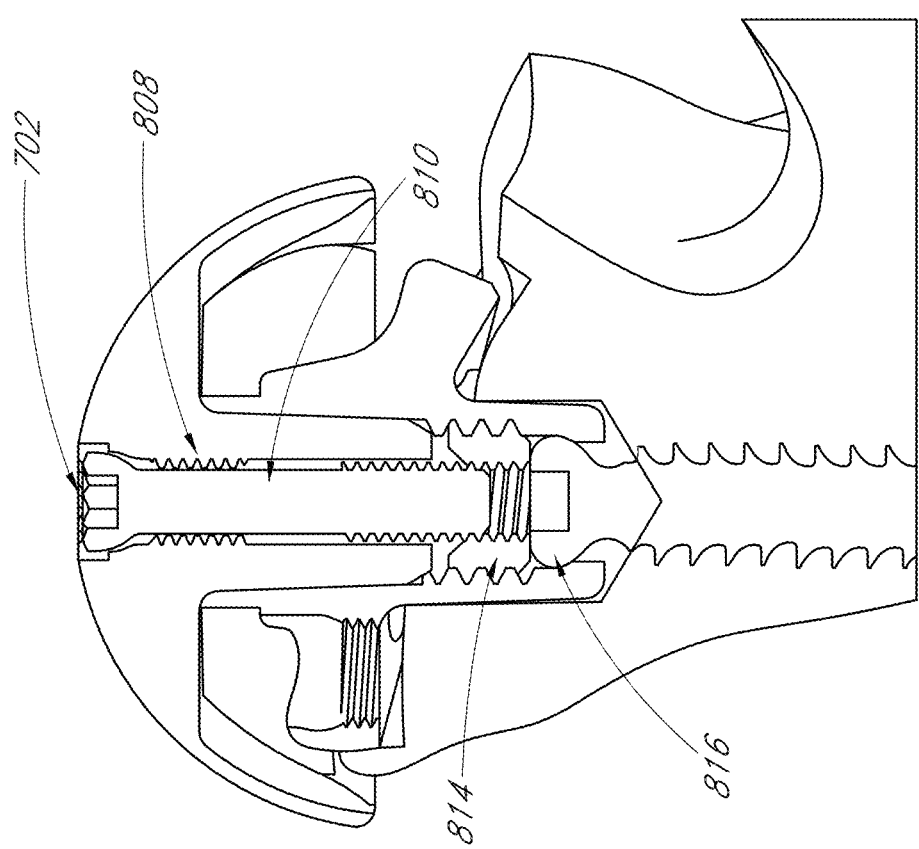
FIG. 8 illustrates a schematic cross-section of a fully assembled glenosphere with a locking bolt, according to some embodiments.

FIG. 8 illustrates a schematic cross-section of a fully assembled glenosphere with a locking bolt, according to some embodiments, along with the baseplate. The glenosphere can include a central channel therethrough including a rotational control feature 702 at, for example, a superior-most portion that can be as described elsewhere herein. The central channel can also include a threaded surface 808 for an inserter/head extractor, such as inferior to the rotational control feature 702, and optionally be configured to accommodate a secondary locking screw at 810, to push and/or rotate with the post of the baseplate. A post of the glenosphere can be placed at least partially within a central channel of the baseplate as illustrated. A central set screw/locking nut 814 can be connected to, and in some cases removably attachable to a central channel, e.g., of the glenoid baseplate, and have an end adjacent or directly touching an end of a central compression screw 816, which can include a diameter of, for example, of about, at least about, or no more than about 4, 4.5, 5, 5.5, 6, 6.5, 7, 7.5, 8, 8.5, 9, 9.5, 10 mm, or more or less, or ranges including any two of the foregoing values. The central compression screw can be configured to angulate with respect to the baseplate, and advantageously allow for the use of a locking screw.

Figures 8A, 8B, 8C, 8D, 8E, 8F:
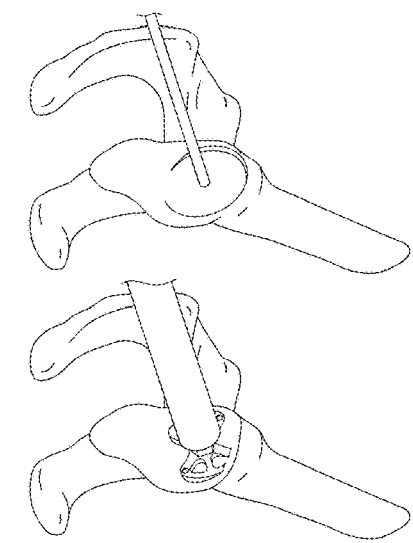
FIGS. 8A-8U illustrate a glenoid surgical technique, according to some embodiments.
Figures 8G, 8H, 8I, 8J, 8K:
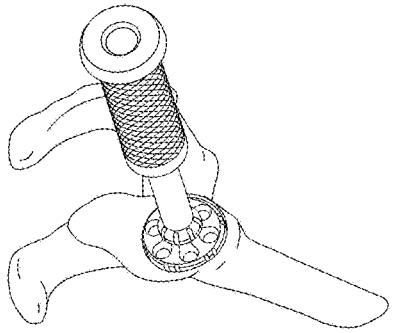
Figure 8P:
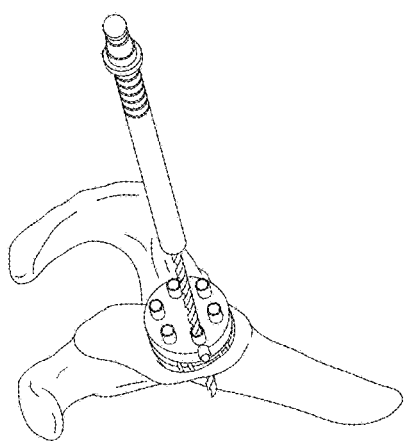
Figure 8O:
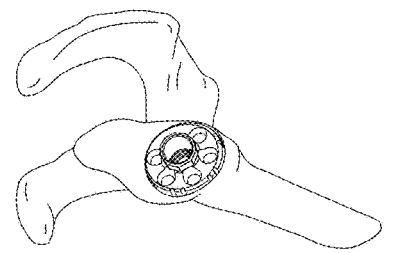
Figure 8N:
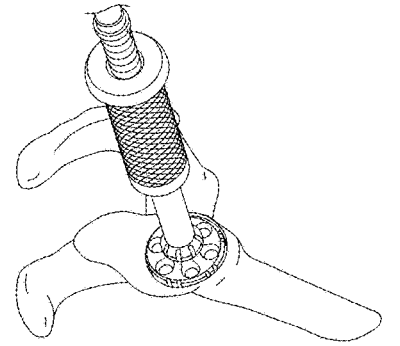
Figure 8M:
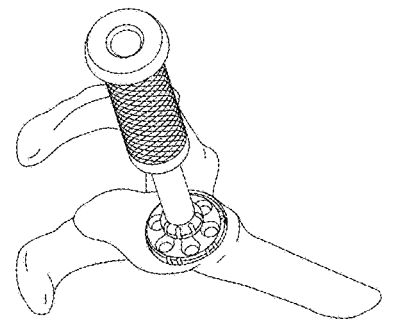
Figure 8L:
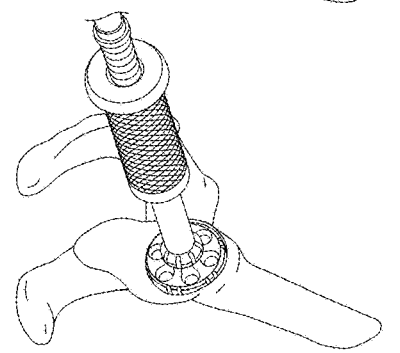
Figure 8U:
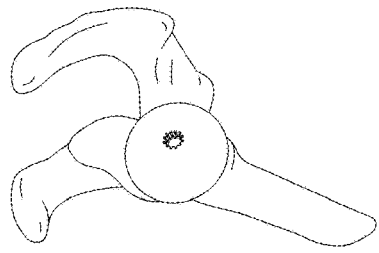
Figure 8T:
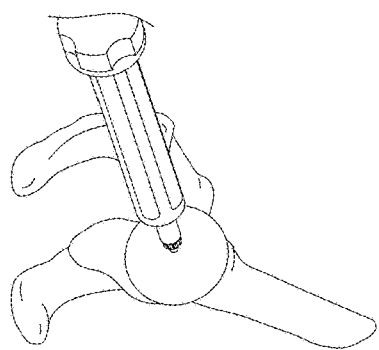
Figure 8S:
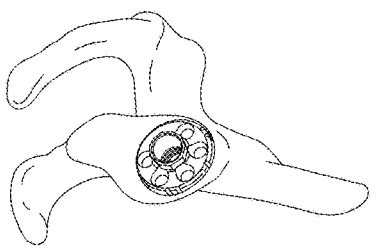
Figure 8R:
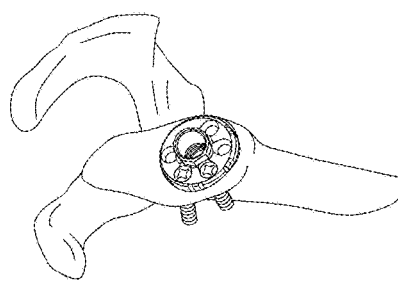
Figure 8Q:
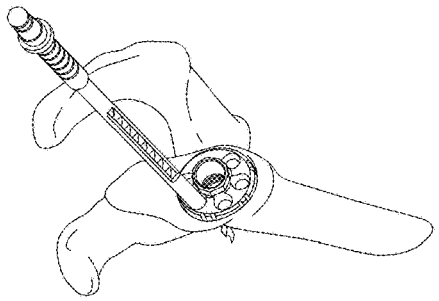

FIGS. 8A-8U illustrate a glenoid surgical technique, according to some embodiments, which can include any number of the following actions. FIG. 8A illustrates a glenoid surface with an A3-E3 defect. A sizer/angle guide can be placed as in FIG. 8B. A wire guide/wire can be placed in FIG. 8C. The wire guide and sizer/angle guide can be removed, as in FIG. 8D. The glenoid surface can then be reamed for the baseplate, as in FIGS. 8E and 8F. The stem drill guide can then be placed and adjusted in FIG. 8G. A hole for a stem can then be drilled in FIGS. 8H and 8I. The baseplate can then be inserted, as shown in FIG. 8J, and the threaded rod removed, as shown in FIG. 8K. A central cavity can be drilled, and the length of a central screw to be placed determined, in FIG. 8L. The drill can be removed in FIG. 8M, and the screw and screwdriver placed through the shaft, and the screw tightened in FIG. 8N. The baseplate inserter handle can be removed in FIG. 8O, and holes can be drilled for the peripheral locking screws in FIG. 8P. Holes can be drilled for variable angle screws, as shown in FIG. 8Q. The peripheral screws can be inserted and tightened in FIG. 8R. The central set screws and secondary locking nuts can be inserted and tightened in FIG. 8S. The glenosphere can be inserted in FIG. 8T, and the locking bolt inserted and tightened in FIG. 8U.

Figure 9:
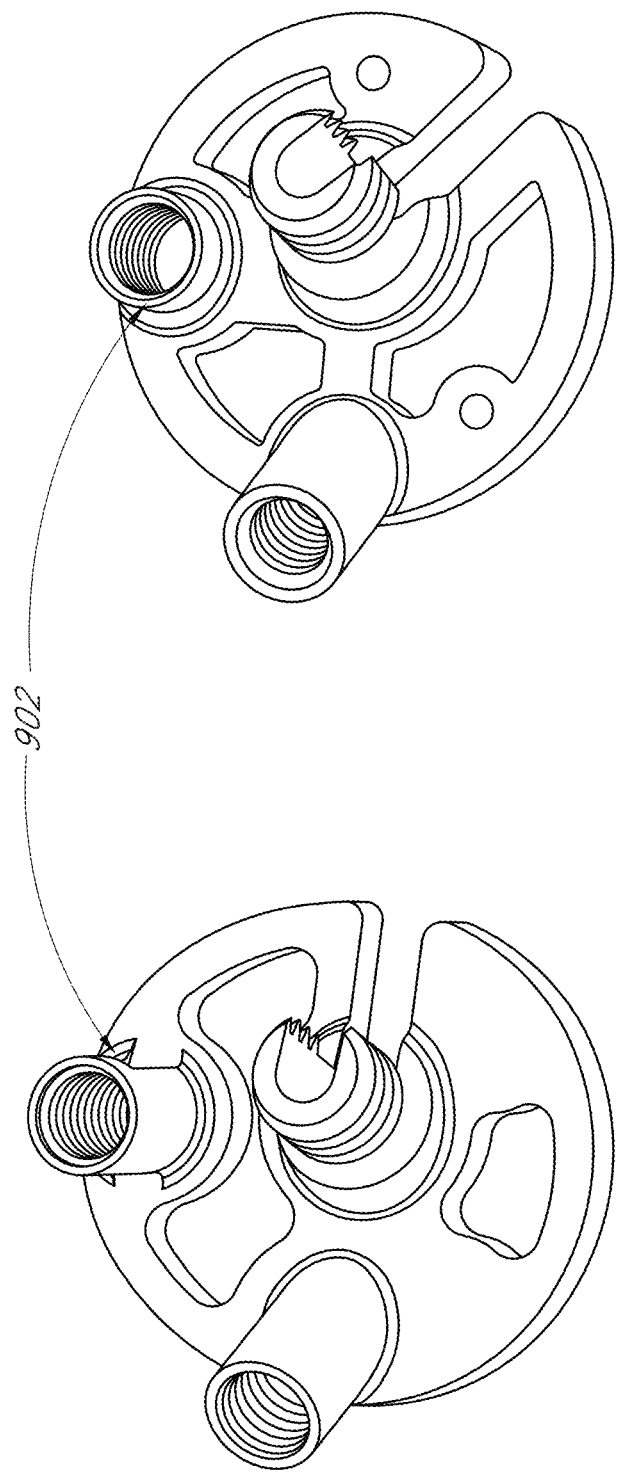
FIG. 9 illustrates an embodiment of a sizer/angle guide.

FIG. 9 illustrates an embodiment of a sizer/angle guide including an inferior tilt mechanism 902. The mechanism could be fixed to a set angle (e.g., about 0, 5, 10, 15, 20, 25 degrees, or ranges including any two of the foregoing values), or adjustable in some embodiments. The mechanism could be round or oval shaped in some embodiments, and include a slot (e.g., posterior or posterior inferior) to allow for removal. The inferior tilt mechanism 902 could include a set screw with a calibrated window, or individual depth screws in some cases.

Figure 10:
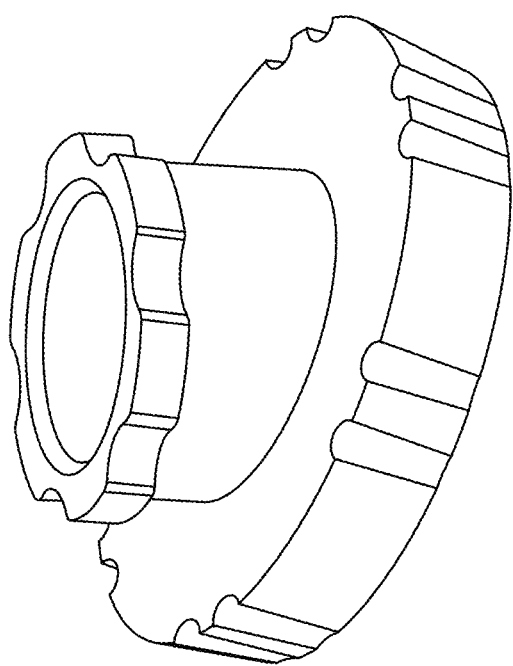
FIG. 10 illustrates an embodiment of a stem drill guide.

FIG. 10 illustrates an embodiment of a stem drill guide, that can include a diameter of about, at least about, or no more than about 18, 19, 20, 21, 22, 23, 24, 25, 26, 27, 28, 29, 30, 31, 32, 33, 34, 35, 36, 37, 38, 39, 40 mm or more or less, or ranges including any two of the foregoing values. The drill guide could include a version angle of, for example, about 0, 5, 10, 15, 20, 25 degrees or more or less, or ranges including any two of the foregoing vales. In some embodiments, the larger the version angle, the more stem tilt is generated as rotation occurs.

Figure 11:
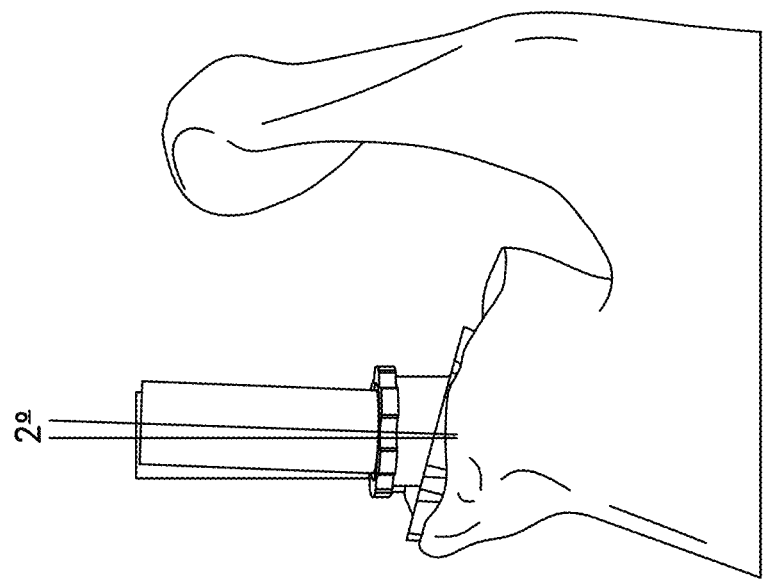
FIG. 11 schematically illustrates a stem angle change with a rotational adjustment.
Figure 11:
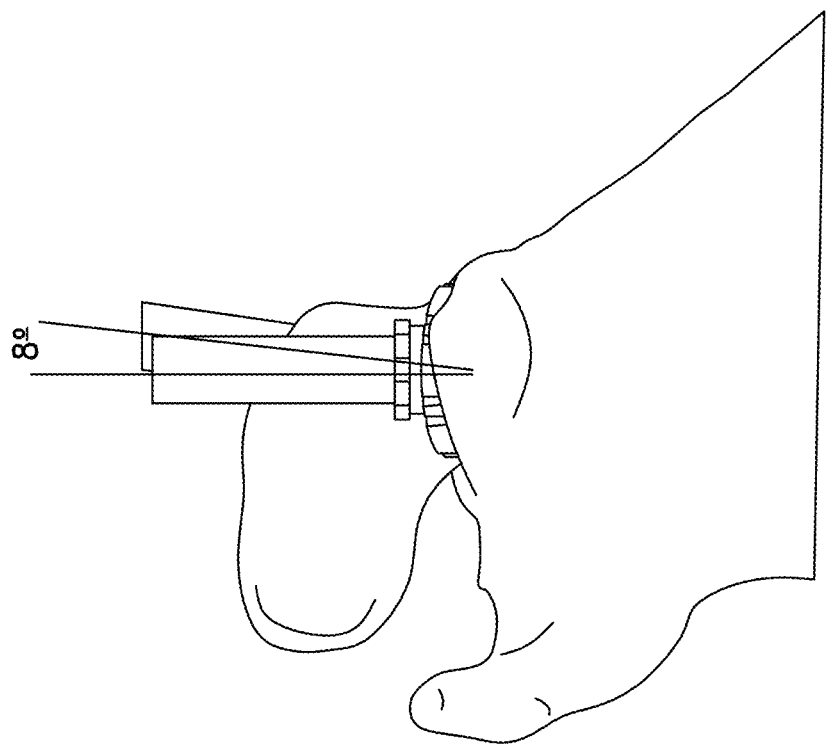

FIG. 11 schematically illustrates a stem angle change with a rotational adjustment (e.g., about 30 degrees), and an angled version plate (e.g., about 15 degrees) as a non-limiting example. Anterior-posterior and inferior-superior views are illustrated.

Figure 12:
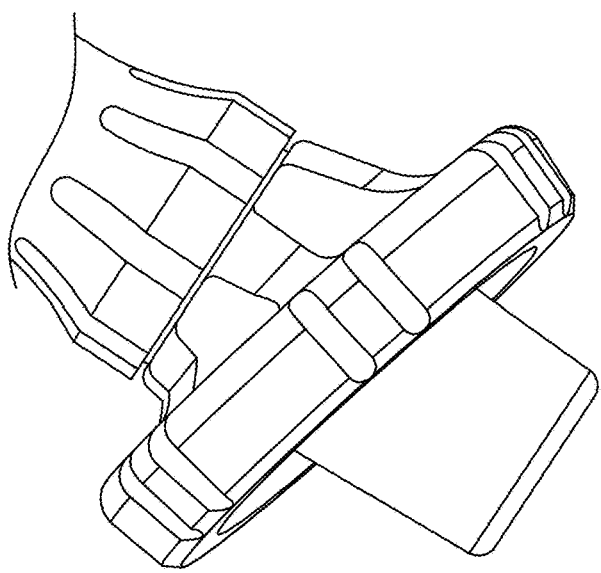
FIG. 12 schematically illustrates views of a glenoid baseplate inserter (alone on the left and together with a baseplate on the right), according to some embodiments.
Figure 12:
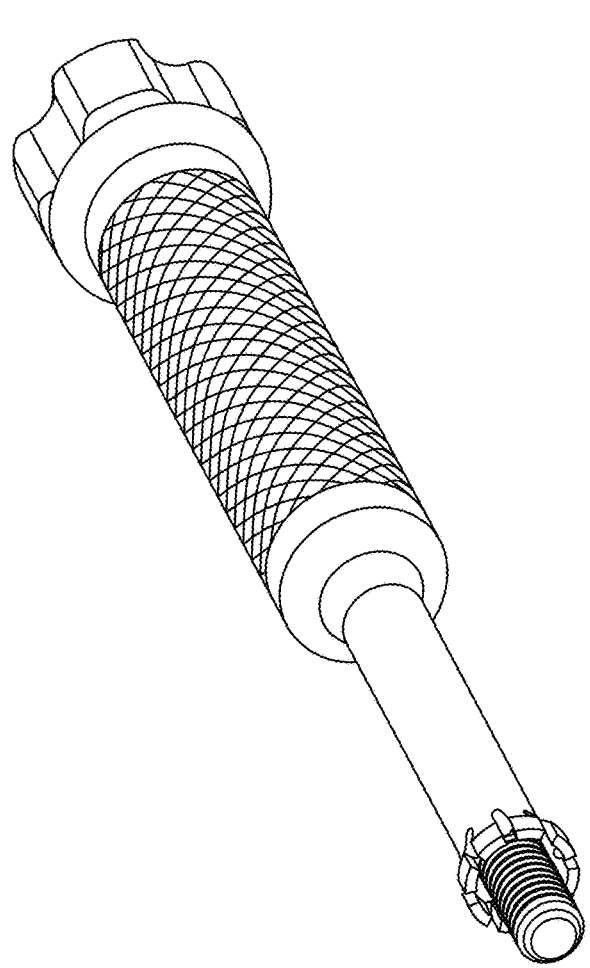

FIG. 12 schematically illustrates views of a glenoid baseplate inserter (alone on the left and together with a baseplate on the right), according to some embodiments. The baseplate inserter can be configured for any number of: positive rotational control; slim design to allow visualization through screw holes to know when seated; and/or a multi-function handle allows for drilling central screw hole, and inserting a central screw.

Figure 13:
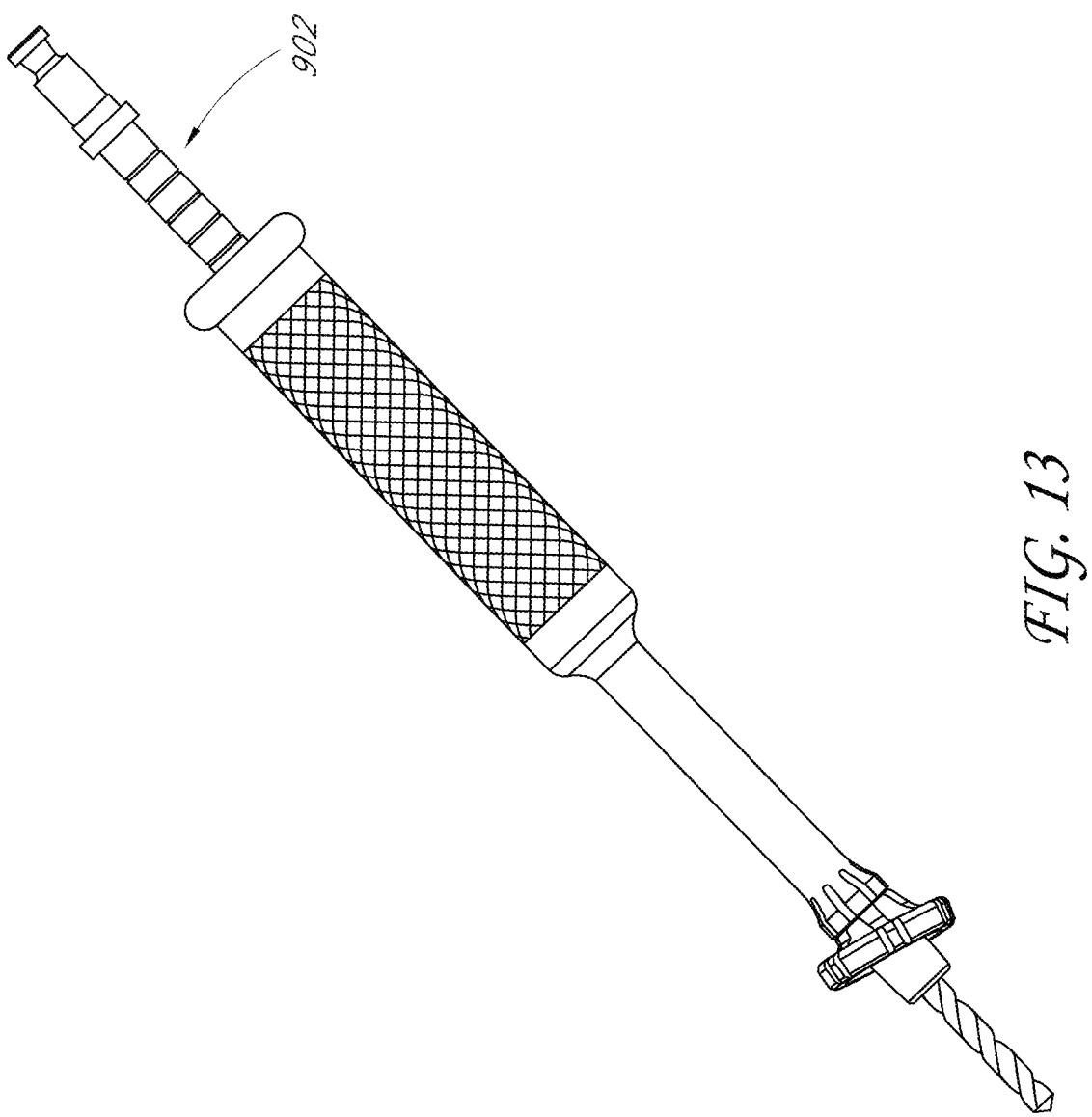
FIG. 13 schematically illustrates views of a calibrated central drill, according to some embodiments.

FIG. 13 schematically illustrates views of a calibrated central drill, according to some embodiments. Calibrated marks/indicia 902 at spaced-apart desired increments (e.g., 5 mm increments in some embodiments) near the proximal end of the instrument can help to determine the length of a central screw that may be needed. The calibration length can start at, for example, about, at least about, or no more than about 15 mm, 20 mm, 25 mm, 30 mm, 35 mm, 40 mm, or more or less, including any two of the foregoing values and may advantageously allow for a surgical step to be cut out.

Figure 14:
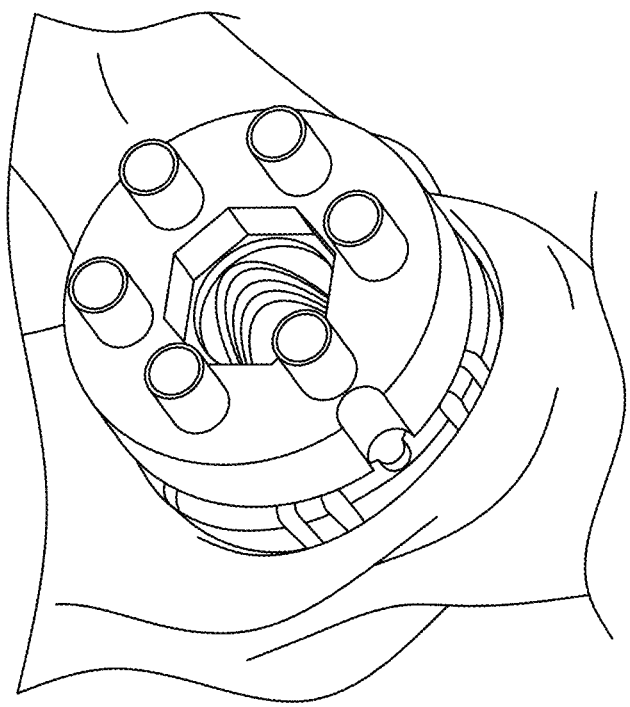
FIG. 14 schematically illustrates views of fixed angle peripheral drill guides, according to some embodiments.
Figure 14:
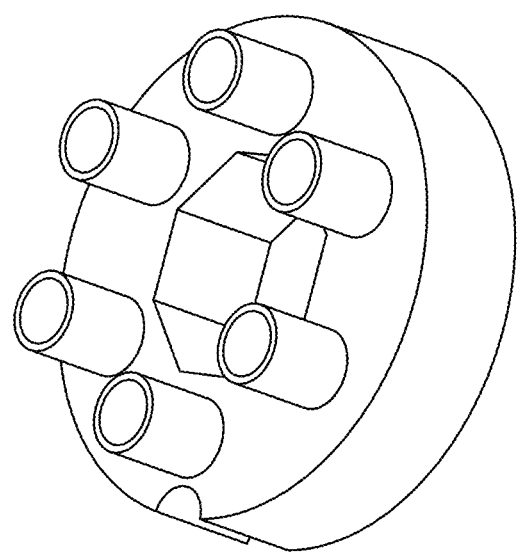

FIG. 14 schematically illustrates views of fixed angle peripheral drill guides, according to some embodiments. The drill guides can be configured to fit over a geometry, such as a polygonal shaped portion (e.g., octagon) on the top of the baseplate, and the operator can then determine which fixed angle screws to drill.

Figure 15:
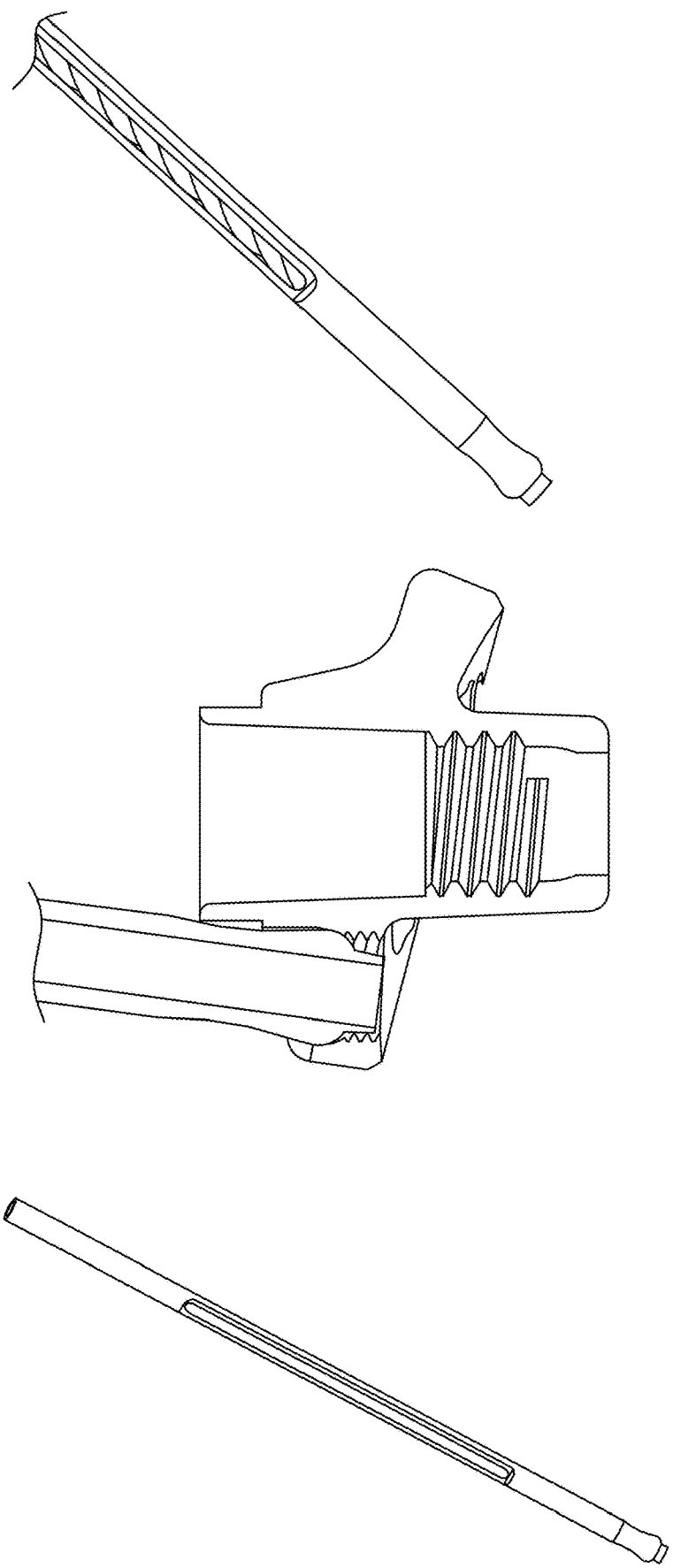
FIG. 15 schematically illustrates views of variable angle peripheral drill guides, according to some embodiments.

FIG. 15 schematically illustrates views of variable angle peripheral drill guides, according to some embodiments.

Figure 16:
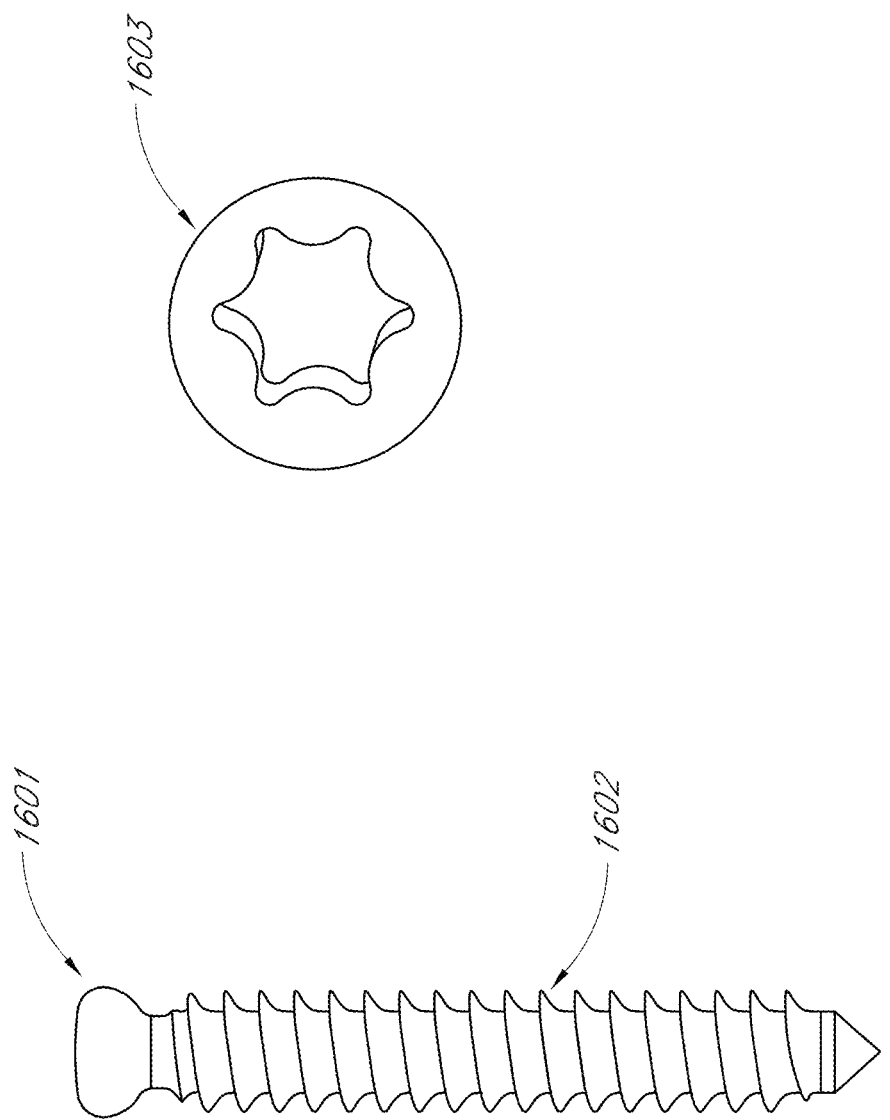
FIG. 16 schematically illustrates side and top views of central screws, according to some embodiments.

FIG. 16 schematically illustrates side and top views of central screws, according to some embodiments, including a head 1601, threaded shaft 1602, and distal tapered portion.

In one embodiment, the screw can have a 6.5 mm head, and 6 mm threaded shaft, although various size ranges and increments are possible, including about, at least about, or no more than about 3, 3.5, 4, 4.5, 5, 5.5, 6, 6.5, 7, 7.5, 8, 8.5, 9, 9.5, 10 mm, or more or less head and/or threaded shaft diameters, or ranges including any two of the foregoing values. In some embodiments, a central screw can include a total or working length of about, at least about, or no more than about 10, 11, 12, 13, 14, 15, 20, 25, 30, 35, 40, 45, 50, 55, 60, 65, 70 mm, or more or less, or ranges including any two of the foregoing values. In some embodiments, anodization of the screw can optionally be present to help differentiate the screws. The screw head could have various internal feature geometries 1603, including a T20 hexalobe configuration in some embodiments.

Figure 17:
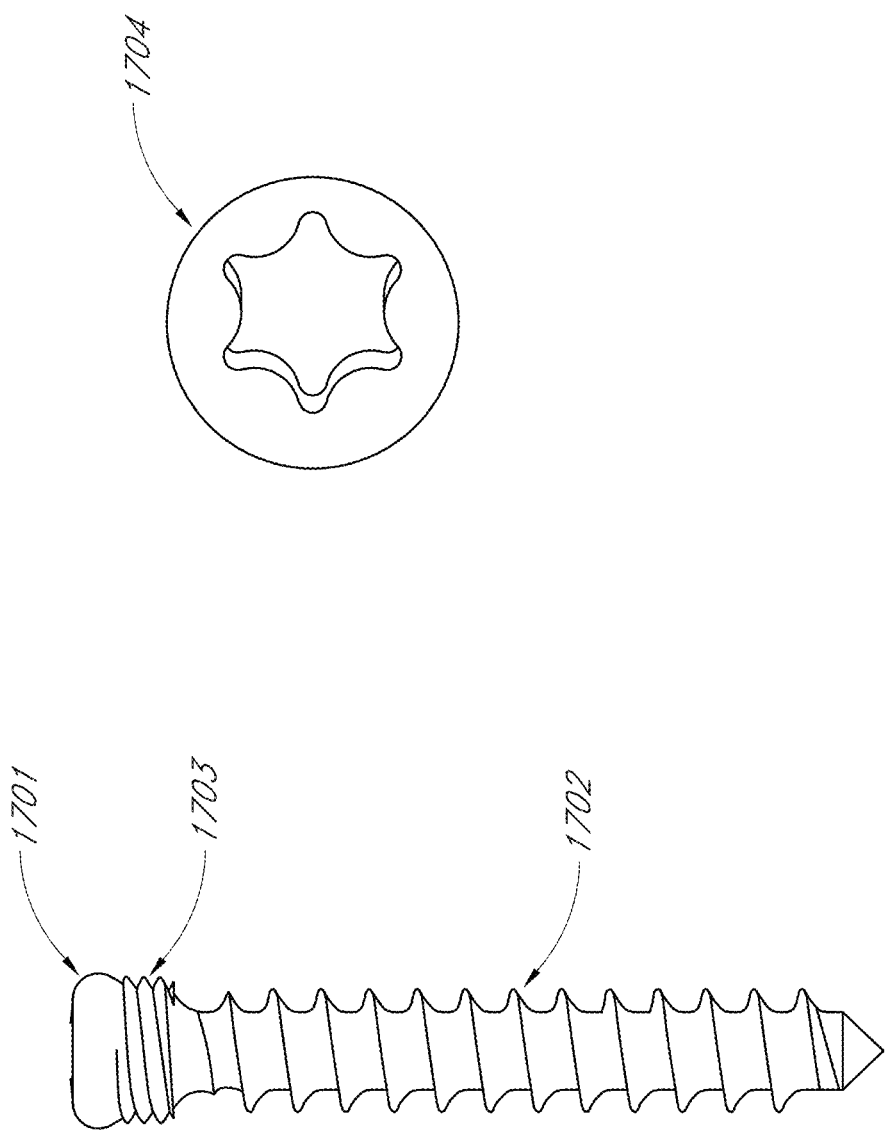
FIG. 17 schematically illustrates side and top views of fixed angle peripheral compression screws, according to some embodiments.

FIG. 17 schematically illustrates side and top views of fixed angle peripheral compression screws, according to some embodiments, including a head 1701, double-lead thread 1703 proximal to a threaded shaft 1702, and distal tapered portion. The screws can be various size ranges and increments, and include T20 hexalobe or other internal head feature geometries 1704 as described elsewhere herein. In one embodiment, the head could be about 5.7 mm in diameter, with a 4.5 mm threaded shaft diameter, or dimensions listed elsewhere herein, such as in connection with FIG. 16 for example.

Figure 18:
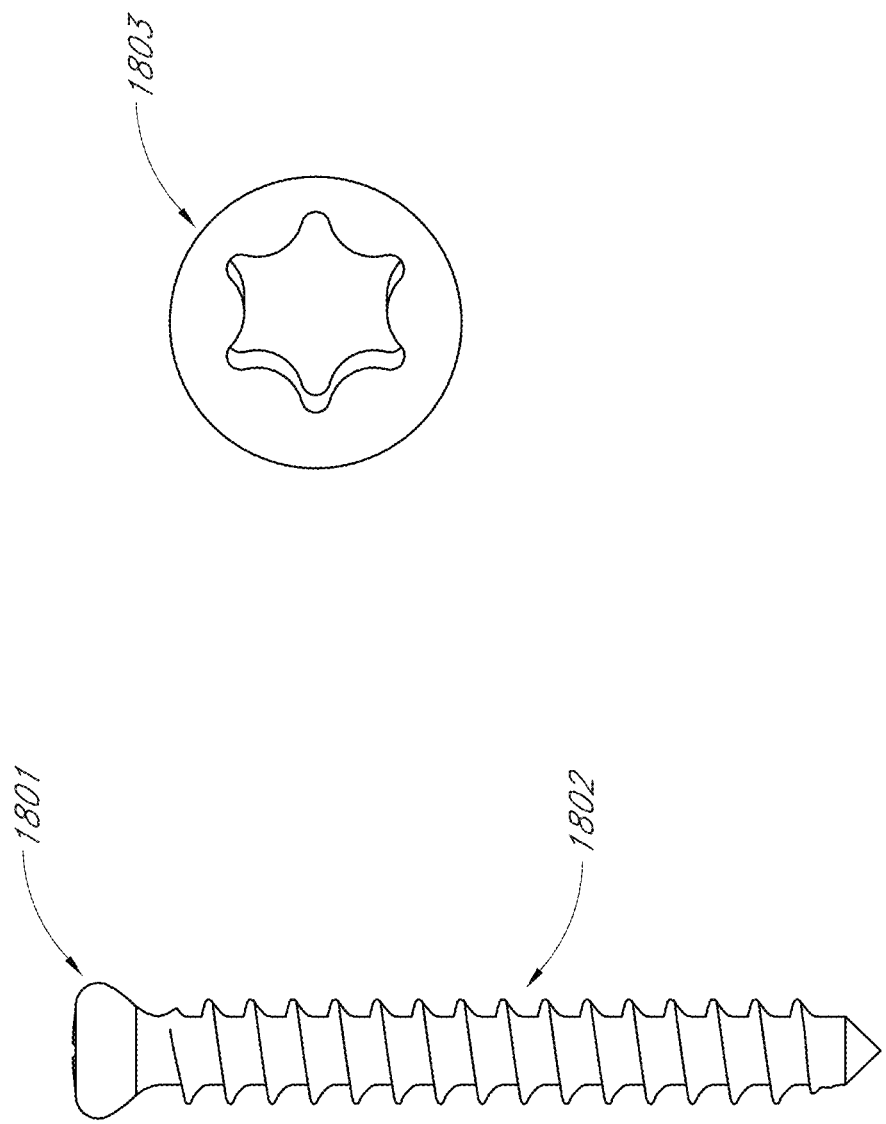
FIG. 18 schematically illustrates side and top views of variable angle peripheral screws, according to some embodiments.

FIG. 18 schematically illustrates side and top views of variable angle peripheral screws, according to some embodiments, including a head 1801, threaded shaft 1802, and distal tapered portion. The screws can be various size ranges and increments, and include T20 hexalobe or other internal head feature geometries 1803 as described elsewhere herein. In one embodiment, the head could be about 5.7 mm in diameter, with a 4.5 mm threaded shaft diameter, or dimensions listed elsewhere herein, such as in connection with FIG. 16 or 17 for example.

Figure 19:
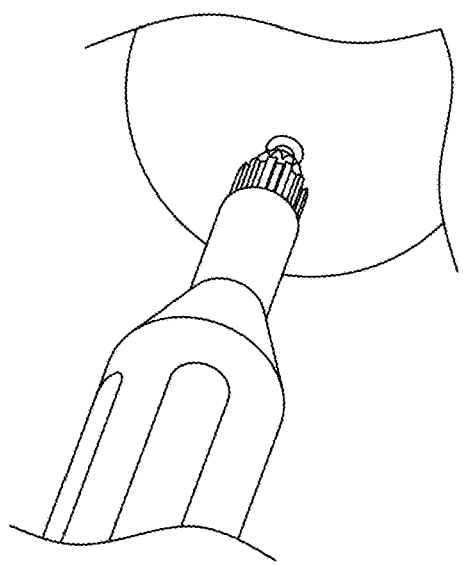
FIG. 19 schematically illustrates views of a glenosphere inserter, according to some embodiments.
Figure 19:
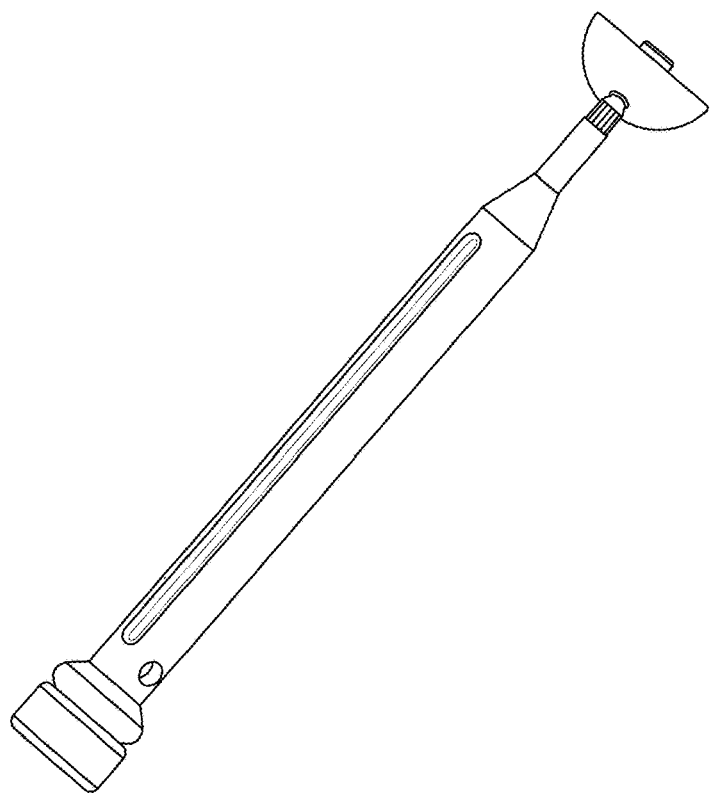

FIG. 19 schematically illustrates views of a glenosphere inserter, according to some embodiments, which can include a distal end with a feature complementary to a spline on the glenosphere, such as described in connection with FIG. 7, for example. The glenosphere inserter can be configured to, for example, advantageously provide positive attachment to the glenosphere; allow for solid rotational control while inserting; and/or may involve a secondary impaction step after removal.

In some embodiments, embodiments of the invention can be used or modified with use with particular advantages of using inset glenoid fixation technology in anatomic shoulder arthroplasty, such as described, for example, in U.S. Pat. Nos. 8,007,538and/or 8,778,028 to Gunther, which are hereby incorporated by reference in their entireties. Furthermore, embodiments of the invention can be used or modified with use with systems and methods as disclosed, for example, in U.S. Pub. No. 2018/0368982 to Ball, which is hereby incorporated by reference in its entirety.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "insetting an implant into a glenoid cavity" includes "instructing the insetting of an implant into the glenoid cavity." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

The invention claimed is:

1. A reverse shoulder implant, comprising:
   a baseplate configured to be secured to a glenoid of a scapular bone of a patient, the baseplate having a lateral end, a medial end, and a baseplate central channel extending through the baseplate from the lateral end to the medial end;
   a central screw configured to at least partially pass through the central channel;
   a locking nut having a cylindrical shape, and an external thread on an outside surface of the locking nut, the locking nut configured to engage the central screw when the central screw and baseplate are implanted within the medical patient, wherein the external thread is configured to couple the locking nut with the baseplate central channel;
   a glenosphere, having a lateral, convex articular surface, and a glenosphere central channel extending from the convex articular surface to an opposite side of the convex articular surface, wherein the glenosphere is configured to interface with the baseplate; and
   a glenosphere screw, sized to pass at least partially within the glenosphere central channel to secure the glenosphere to the locking nut.

2. The reverse shoulder implant of claim 1, wherein the glenosphere is configured to at least partially surround an external surface of the baseplate.

3. The reverse shoulder implant of claim 1, wherein the baseplate has a circular shape.

4. The reverse shoulder implant of claim 1, wherein the glenosphere is configured to surround the baseplate.

5. The reverse shoulder implant of claim 1, wherein the glenosphere is configured to be secured to the baseplate with a Morse taper.

6. The reverse shoulder implant of claim 1, wherein a diameter of the locking nut is greater than a length of the locking nut.

7. The reverse shoulder implant of claim 1, wherein the locking nut comprises a rotational control feature configured to receive a tool to enable twisting of the locking nut to secure it to the central screw.

8. The reverse shoulder implant of claim 1, wherein the central screw has a length of about 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, or 15mm.

9. The reverse shoulder implant of claim 1, wherein the central channel defines a surface integral with the central screw.

10. The reverse shoulder implant of claim 1, wherein the central screw includes a rotational control feature.

11. The reverse shoulder implant of claim 1, wherein the central screw comprises a central channel configured to house a primary screw.

12. A reverse shoulder implant, comprising:
    a baseplate configured to be secured to a glenoid of a scapular bone of a patient, the baseplate having a lateral end, a medial end, and a baseplate central channel extending through the baseplate from the lateral end to the medial end;
    a central screw configured to at least partially pass through the central channel;
    a locking nut having a cylindrical shape, and an external thread on an outside surface of the locking nut, the locking nut configured to engage the central screw when the central screw and baseplate are implanted within the medical patient, wherein the external thread is configured to engage the baseplate central channel; and
    a glenosphere, having a lateral, convex articular surface, and a glenosphere central channel extending from the convex articular surface to an opposite side of the convex articular surface, wherein the glenosphere is configured to interface with the baseplate; and
    a glenosphere screw, sized to pass at least partially within the glenosphere central channel to secure the glenosphere to the locking nut.

13. The reverse shoulder implant of claim 12, wherein the glenosphere is configured to at least partially surround an external surface of the baseplate.

14. The reverse shoulder implant of claim 12, wherein the baseplate has a circular shape.

15. The reverse shoulder implant of claim 12, wherein the glenosphere is configured to surround the baseplate.

16. The reverse shoulder implant of claim 12, wherein the glenosphere is configured to be secured to the baseplate with a Morse taper.

17. The reverse shoulder implant of claim 12, wherein a diameter of the locking nut is greater than a length of the locking nut.

18. The reverse shoulder implant of claim 12, wherein the locking nut comprises a rotational control feature configured to receive a tool to enable twisting of the locking nut to secure it to the central screw.

19. The reverse shoulder implant of claim 12, wherein the central screw has a length of about 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, or 15mm.

20. The reverse shoulder implant of claim 12, wherein the central channel defines a surface integral with the central screw.

21. The reverse shoulder implant of claim 12, wherein the central screw includes a rotational control feature.

22. The reverse shoulder implant of claim 12, wherein the central screw comprises a central channel configured to house a primary screw.

* * * * *